(12) United States Patent
Santos

(10) Patent No.: US 11,910,876 B2
(45) Date of Patent: Feb. 27, 2024

(54) WRAP COMPRESSION SYSTEM

(71) Applicant: Under Armour, Inc., Baltimore, MD (US)

(72) Inventor: Craig Santos, Portland, OR (US)

(73) Assignee: Under Armour, Inc., Baltimore, MD (US)

( * ) Notice: Subject to any disclaimer, the term of this patent is extended or adjusted under 35 U.S.C. 154(b) by 134 days.

(21) Appl. No.: 16/880,628

(22) Filed: May 21, 2020

(65) Prior Publication Data

US 2021/0361024 A1 Nov. 25, 2021

(51) Int. Cl.
| | |
|---|---|
| *A43B 7/14* | (2022.01) |
| *A61F 13/08* | (2006.01) |
| *A61F 5/01* | (2006.01) |
| *A43B 7/1455* | (2022.01) |

(52) U.S. Cl.
CPC ............. *A43B 7/14* (2013.01); *A61F 5/01* (2013.01); *A61F 5/0111* (2013.01); *A61F 13/085* (2013.01)

(58) Field of Classification Search
CPC ...... A61F 5/0111; A61F 13/085; A61F 13/08; A61F 5/0195; A61F 13/067; A61F 5/01–03; A61F 13/06–148; A61H 2011/005; A61H 11/00–02; A43B 7/00; A43B 7/14–38
See application file for complete search history.

(56) References Cited

U.S. PATENT DOCUMENTS

| | | | |
|---|---|---|---|
| 4,910,802 A | 3/1990 | Malloy | |
| 8,082,762 B2 | 12/2011 | Burr | |
| 8,707,468 B2 | 4/2014 | Reynolds et al. | |
| 9,271,890 B1 | 3/2016 | Pamplin et al. | |
| 9,326,911 B2 | 5/2016 | Wyatt et al. | |
| 10,188,152 B2 | 1/2019 | Stasey et al. | |
| 10,441,491 B2 | 10/2019 | Wyatt et al. | |

(Continued)

FOREIGN PATENT DOCUMENTS

| | | |
|---|---|---|
| CN | 109198749 | 1/2019 |
| KR | 101331858 | 11/2013 |

(Continued)

OTHER PUBLICATIONS

U.S. Appl. No. 17/019,171, filed Sep. 11, 2020.

*Primary Examiner* — Michelle J Lee

(74) *Attorney, Agent, or Firm* — Edell, Shapiro & Finnan, LLC

(57) ABSTRACT

A compression appliance includes a textile-based wrap, an electronic assembly, and wiring comprising a single wire looped through the length of the wrap. The wiring comprises shape changing materials that are used to apply controllable intermittent sequential compression or constriction pressure to a body portion of a person when the compression appliance is wrapped around the body portion. The appliance can incorporate a pre-tensioning element that applies a known initial tension to the shape changing material prior to activation of a compression cycle. The wire can be then actuated according to a compression protocol to sequentially contract and release the wire. The proposed wiring and component configuration will need access to lower power and a reduced volume of hardware as compared to conventional compression appliances.

20 Claims, 14 Drawing Sheets

(56) References Cited

U.S. PATENT DOCUMENTS

| | | | |
|---|---|---|---|
| 2014/0257156 A1* | 9/2014 | Capra | A43C 11/165 |
| | | | 602/5 |
| 2015/0065930 A1 | 3/2015 | Wyatt et al. | |
| 2016/0074234 A1* | 3/2016 | Abichandani | G05B 15/02 |
| | | | 601/84 |
| 2016/0120734 A1 | 5/2016 | Ishikawa et al. | |
| 2016/0175179 A1* | 6/2016 | Pamplin | A61H 7/007 |
| | | | 601/84 |
| 2016/0374886 A1 | 12/2016 | Wyatt et al. | |
| 2017/0202271 A1 | 7/2017 | Stasey et al. | |
| 2017/0202276 A1 | 7/2017 | Wyatt et al. | |
| 2017/0252252 A1* | 9/2017 | Wyatt | A63B 69/36 |
| 2017/0304139 A1* | 10/2017 | Ross | A61H 11/00 |
| 2017/0318908 A1 | 11/2017 | Wyatt et al. | |
| 2018/0055009 A1 | 3/2018 | Wyatt et al. | |
| 2018/0177677 A1* | 6/2018 | Pamplin | A61H 7/001 |
| 2019/0133215 A1 | 5/2019 | Whalen | |
| 2019/0261744 A1 | 8/2019 | Wyatt et al. | |
| 2019/0274372 A1* | 9/2019 | Rizzo | A61H 11/00 |

FOREIGN PATENT DOCUMENTS

| | | | | |
|---|---|---|---|---|
| KR | 20150118683 A | * | 10/2015 | |
| WO | 200462403 | | 7/2004 | |
| WO | WO-2015030267 A1 | * | 3/2015 | A61F 5/028 |

\* cited by examiner

WRAP COMPRESSION SYSTEM

BACKGROUND

Compression appliances, including those provided as wraps, coverings, garments (e.g., articles of footwear and clothing), devices, equipment, and other articles are generally comprised of one or more stretchable fabric segments characterized by a particular modulus of elasticity. When a wearer places the appliance on his or her body, the fabric stretches around various body parts and applies a compressive force to the body parts. These compression appliances are sometimes used to facilitate post workout or post game recovery of particular body parts. For example, an athlete experiencing trauma to a knee during a sporting event may wear compression leggings or wraps to help reduce swelling around the knee. The use of compression appliances is sometimes preferred over the more traditional use of ice bags to control swelling, since compression appliances may be used over a relatively long period without relative discomfort, dripping ice bags or other mess and inconvenience commonly associated with ice treatment.

Compression appliances can aid recovery for athletes across various sporting disciplines. Growing data indicates compression appliances improve recovery because of their favorable biochemical and physiological benefits, as well as a wide range of functional recovery benefits. For example, following exhaustive exercise, participants frequently experience significant delayed onset muscle soreness (DOMS). This is typically present 1-5 days after exertion and is closely correlated with ultrastructural muscle damage as demonstrated on post-exertion muscle biopsy. This has also been indicated by increased levels of creatinine kinase (CK), interleukin 6 (IL-6), and lactate levels following exercise. Similarly, following endurance exercise, there is considerable venous pooling in the lower limbs that can leads to a dramatic fall in venous return and an increase in the time to excretion of muscle damage waste products such as CK and lactate. These "waste" products are thought to cause damage to healthy muscle cells.

Compression appliances have been shown to have beneficial effects on self-reported DOMS and a decrease in measured levels of CK and lactate. This indicates enhanced repair of the body's musculature at low levels of tissue damage. Furthermore, they have a well-documented effect of increasing lower-limb venous return and decreasing venous pooling post-exercise, which has been associated with dramatic increases in lower-limb oxygenation. It has also been shown that lower-limb compression appliances reduce recovery heart rate immediately following exercise, further aiding their potential use as a recovery strategy. Compression appliances have also been shown to augment lower-limb "muscle pump" action thereby increasing cardiac venous return in preparation for renal perfusion and blood-borne waste product removal. It is thought that compression appliances achieve this effect by creating an external pressure gradient, which reduces available space for muscle edema to occur and thereby reduces the secondary inflammatory response. If compression socks produce beneficial effects on recovery following exhaustive exercise, they could provide a benefit in recovery from both training and competition. Improvements in compression systems would aid runners and other athletes, strength and conditioning specialists, athletic trainers, and coaches to increase the training efficiency of their programs, as well as laypersons suffering from health and cosmetic problems (e.g., relatively immobile patients, such as post-operative patients, the bedridden, and those individuals suffering from lymphedema and diabetes can be prone to deep vein thrombosis (DVT)).

While compression appliances are sometimes used to treat injuries and trauma, traditional compression appliances have certain downsides. In particular, traditional compression appliances tend to provide different amounts of pressure to different parts of the body. Some compression appliances are simply cut in a manner that randomly applies different levels of compressive pressure to various body parts. This uneven compression is not ideal for recovery following physical trauma experienced from normal wear and tear from working out, as certain body parts may not be properly supported by the garment in a manner that promotes healing. Of particular need is a device that is comfortable, lightweight, easy to transport, and mobile. Current technology uses plastic wrapped around the extremity causing enhanced perspiration and discomfort, so a device that is comfortable and mobile will increase athlete and patient compliance with a treatment regimen. In patients, such compliance may reduce the risk of DVT and/or related peripheral vascular disease (PVD), or venous flow anomalies which could have positive economic impact on costs of healthcare.

In view of the foregoing, it would be desirable to provide a compression appliance that offers a relatively consistent and precise compression force to substantially the entire body while remaining lightweight and portable. It would also be advantageous if such garment could be manufactured to provide consistent compression performance across a wide variety of body types. Furthermore, it would be advantageous if such garment could be easily worn following a workout or other physical exertion activity in order to promote a relatively quick recovery with improved vitality, reduced swelling, increased power output and reduced muscle damage.

SUMMARY

In one aspect, a wearable compression appliance includes an elongated wrap portion extending between a first end portion and a second end portion of the compression appliance, where the wrap portion includes a first zone and a second zone. The compression appliance also includes a first wire element, the first wire element being embedded in the wrap portion in a looped arrangement such that the first wire element includes both an upper wire segment that extends across a length of the wrap portion and a lower wire segment that extends along the length of the wrap portion, and the upper wire segment is spaced apart from the lower wire segment. Furthermore, a first distance between the upper wire segment and lower wire segment in the first zone is smaller than a second distance between the upper wire segment and lower wire segment in the second zone.

In another aspect, a method of using a compression appliance includes a first step receiving a selection of a first compression setting, and a second step of generating a compression profile corresponding to the first compression setting that is configured for actuation using a single wire element. A third step includes repeatedly actuating, in a pattern and for a duration corresponding to the generated compression profile, a single shape memory alloy wire element that is embedded in a wrap portion of the compression appliance. Finally, a fourth step includes causing the wire element to repeatedly constrict and expand.

In another aspect, the present disclosure is directed to article of footwear that includes a sole structure and an upper secured to the sole structure and configured to receive a foot of a wearer. In addition, a single wire element extends in multiple circuits around the article of footwear through both the upper and sole structure to provide at least two loops, resulting in at least four spaced apart wire segments (made of the single continuous wire element) that encircle the article of footwear.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

DETAILED DESCRIPTION

Figure 1:
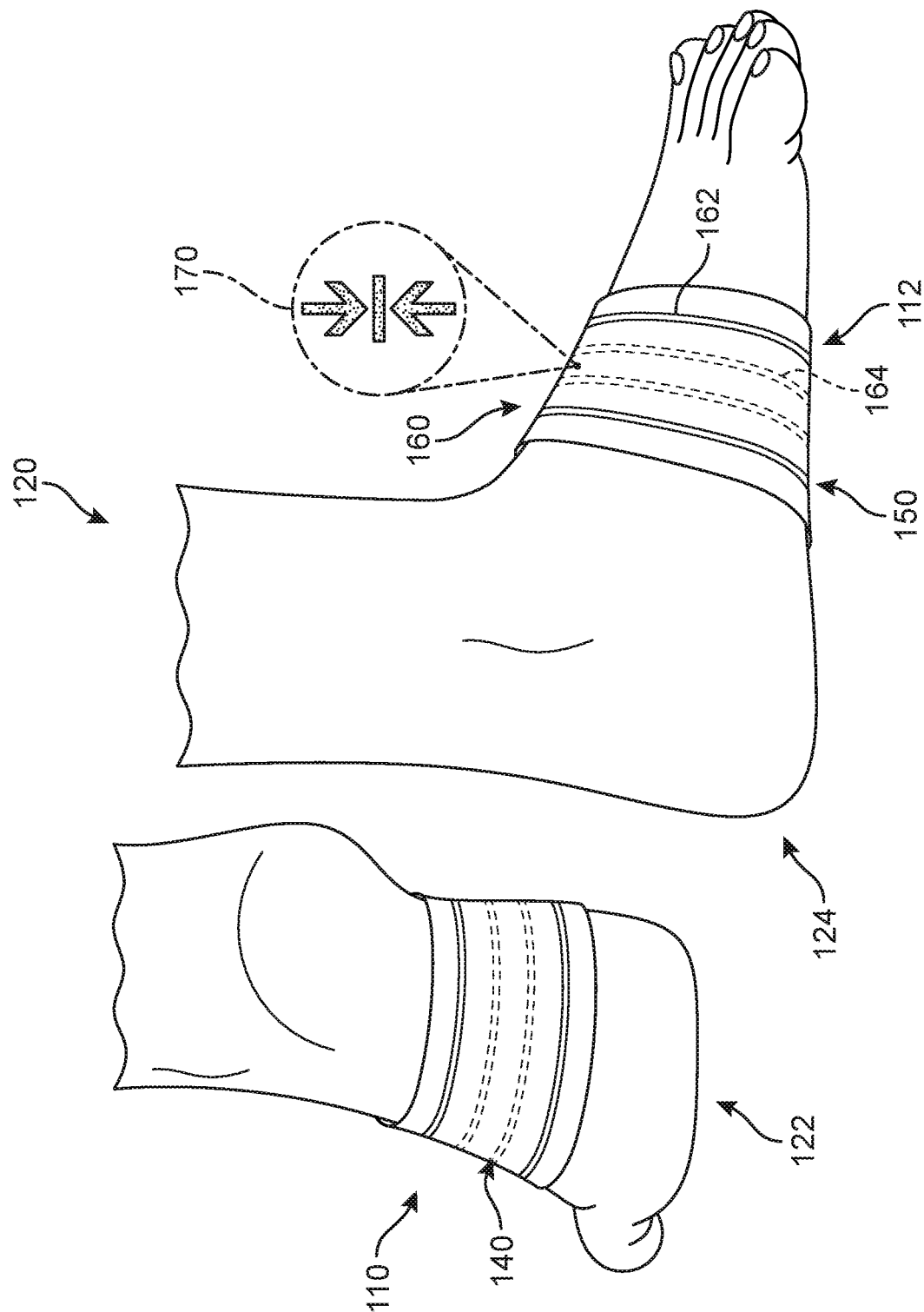
FIG. 1 is an example of a pair of compression appliances as worn on the feet of a user.

Compression appliances are typically static devices. In other words, they do not move on their own. Compression appliances that are not static devices, and thus that can compress and relax on their own, are bulky and slow because they are driven by gases, such as air, or fluids, such as water. The proposed embodiments are related to an appliance that includes one or more shape changing materials that are incorporated into compression textiles or fabrics. The shape changing materials are used to apply controllable intermittent sequential compression or constriction pressure to a body portion of a person. The appliance can incorporate a pre-tensioning element that applies a known initial tension to the shape changing material prior to activation of a compression cycle. For example, the pre-tensioning element can include an elastic band that is connected across the shape changing material element, such as a shape memory metal alloy (SMA) wire or other wire. When the compression device is worn on the body of the user, the pre-tensioning element is placed into tension, which also applies a pre-tension to the wire. The wire is then actuated according to a compression protocol to sequentially contract and release the wire. The compression protocol applied to actuate the wiring, as well as the amount of pre-tension provided by the pre-tensioning element can be calibrated to the particular article of clothing in which the device is integrated. The proposed wiring and component configuration will need access to lower power and a reduced volume of hardware as compared to conventional compression appliances.

Embodiments of this compression wiring configuration can be integrated into articles such as articles of footwear, articles of apparel (e.g., clothing), as well as accessories and/or equipment. For the purposes of general reference, an article is any item designed to be worn by or on a user, or act as an accessory. In some embodiments, an article may be an article of footwear, such as a shoe, sandal, boot, etc. In other embodiments, an article may be an article of apparel, such as a wrap, sleeve, or garment, including shirts, pants, jackets, socks, undergarments, or any other conventional item. In still other embodiments, an article may be an accessory such as a hat, glove, or bag worn by the wearer.

In different embodiments, the proposed appliances include an elongated fabric or textile that incorporates only a single wire yet continues to provide the expected benefits of a compressive protocol associated with multiple wires. The single wire extends from one end of the article and loops back toward its starting point. One length of the wire is axially spaced from another length. When the article overlaps itself, the two wire regions form two effective loops that can perform in a manner similar to a plurality of separate wires. In addition, because these wires typically include a limited coefficient of contraction, the repeated wrapping produces a magnified compressive effect relative to a single layer wrap. Furthermore, by reducing the number of wires that would traditionally be integrated in the article, the proposed systems and methods significantly minimize the amount of power needed, and rely on fewer components for assembly, thereby reducing cost and improving efficiency.

To assist and clarify the subsequent description of various embodiments, various terms are defined herein. Unless otherwise indicated, the following definitions apply throughout this specification (including the claims). For consistency and convenience, directional adjectives are employed throughout this detailed description corresponding to the illustrated embodiments.

Some of the proposed embodiments are directed to a compression appliance for use with or around a person's foot. For purposes of general reference, a foot may be divided into three regions: a forefoot region, a midfoot region, and a heel region. The forefoot region may be generally associated with the toes and joints connecting the metatarsals with the phalanges. The midfoot region may be generally associated with the arch of a foot, including the instep. Likewise, the heel region or "hindfoot" may be generally associated with the heel of a foot, including the calcaneus bone. For purposes of this disclosure, the following directional terms, when used in reference to an article to be worn or wrapped on a foot ("article of footwear"), shall refer to footwear when sitting in an upright position, with the sole facing the ground, that is, as it would be positioned when worn by a wearer standing on a substantially level surface.

The term "longitudinal," as used throughout this detailed description and in the claims, refers to a direction extending along the length of a component or foot. For example, a longitudinal direction of an article of footwear extends from the forefoot region to the heel region of article of footwear. The term "forward" or "front" is used to refer to the general direction in which the toes of a foot point, and the term "rearward" or "back" is used to refer to the opposite direction, i.e., the direction in which the heel of the foot is facing.

The term "lateral direction," as used throughout this detailed description and in the claims, refers to a side-to-side direction extending along the width of a component or foot. In other words, the lateral direction may extend between a medial side and a lateral side of an article of footwear, with the lateral side being the surface that faces away from the other foot, and the medial side being the surface that faces toward the other foot.

The term "vertical," as used throughout this detailed description and in the claims, refers to a direction generally perpendicular to both the lateral and longitudinal directions. For example, in cases where an article of footwear or foot is planted flat on a ground surface, the vertical direction may extend from the ground surface upward. It will be understood that each of these directional adjectives may be applied to individual components of an article of footwear. The term "upward" refers to the vertical direction heading away from a ground surface, while the term "downward" refers to the vertical direction heading toward the ground surface. Similarly, the terms "top," "upper," and other similar terms refer to the portion of an object substantially furthest from the ground in a vertical direction, and the terms "bottom," "lower," and other similar terms refer to the portion of an object substantially closest to the ground in a vertical direction.

It will be understood that the forefoot region, the midfoot region, and the heel region are only intended for purposes of description and are not intended to demarcate precise regions of an article of footwear or foot. For example, in some cases, one or more of the regions may overlap. Likewise, the medial side and the lateral side are intended to represent generally two sides, rather than precisely demarcating an article of footwear or foot into two halves. In addition, the forefoot region, the midfoot region, and the heel region, as well as the medial side and the lateral side, may also be applied to individual components of an article of footwear, including a sole structure, an upper, a lacing system, and/or any other component associated with the article.

For purposes of this disclosure, the term "fixedly attached" shall refer to two components joined in a manner such that the components may not be readily separated (for example, without destroying one or both of the components). Exemplary modalities of fixed attachment may include joining with permanent adhesive, rivets, stitches, nails, staples, welding or other thermal bonding, or other joining techniques. In addition, two components may be "fixedly attached" by virtue of being integrally formed, for example, in a molding process.

For purposes of this disclosure, the term "removably attached" or a "releasable" fastener mechanism shall refer to the joining of two components in a manner such that the two components are secured together, but may be readily detached from one another. Examples of removable attachment mechanisms may include hook and loop fasteners, friction fit connections, interference fit connections, threaded connectors, cam-locking connectors, and other such readily detachable connectors. Similarly, "removably disposed" shall refer to the assembly of two components in a non-permanent fashion.

The term "wire" includes a single elongated fiber, filament, or monofilament that comprise at least a portion of a metal element, as well as an ordered flexible assemblage of textile fibers having a high ratio of length to diameter and normally used as a unit (e.g., slivers, roving, single yarns, plies yarns, cords, braids, ropes, rods, etc.) that include or are made of one or more metal elements. Furthermore, for purposes of this application, a wire refers to a long thin piece of metal that is used to carry electric current, and in some cases, to experience and manifest patterns of contraction and release.

Referring to FIG. 1, for purpose of introduction, one example of a compression appliance is depicted. A first compression appliance may be constructed to be applied to virtually any part or portion of the body of a human or other living organism, including a user's foot, arm, calf, and other portions of the user's body. A first compression appliance ("first appliance") 110 and a second compression appliance ("second appliance") 112 are being worn by a first user 120 in FIG. 1. The first appliance 110 is wrapped around a portion of first user's left foot 122 and the second appliance 112 is wrapped around a portion of first user's right foot 124. In other examples, an end-user may only utilize a single compression appliance at a time. Each of the compression appliances can further include a controller assembly (see FIG. 2) and a textile or fabric wrap ("wrap"), as well other plurality of electrical and mechanical components that are integrated into or connected to the wrap. For example, the wrap can incorporate or be connected to processing circuitry configured to receive a selection for predetermined compression profiles and, in some cases, heat settings, as well as other functionality, including the ability to energize a shape changing material engine, monitor battery usage and charge, keep time of an active session, store engine usage, and log any errors. In addition, the compressive appliance includes a power source (e.g., a lithium ion battery) or an input to receive energy in order to power its electronic components.

In different embodiments, wraps may be formed of a generally inelastic or only moderately "stretchable" material that is suited for contact with the skin of the user. The material of the fabric body may be a breathable material to reduce perspiration or may be a generally impermeable material to enhance heating of the body part under compression treatment. In one embodiment, the wrap can be a compressible body having a thickness to accommodate the shape-changing elements described herein and may include one or more pockets or sleeves to receive and retain processing circuitry, power source, and/or a controller assembly. In some embodiments, components can be sewn into the wrap. In one embodiment, the wrap comprises an elastic three-layer material made of polyurethane foam with smooth knit material bonded on both sides. The wrap material can be understood to have a thickness to accommodate the shape-changing wire element(s) described herein.

As a general matter, a wrap can utilize shape changing materials to apply compression. It may also contain material that, separate from or the same as the shape changing material, conducts and releases heat. For example, the shape changing materials can include a shape memory metal alloy implemented as a shape memory wire (e.g., Nitinol wire). The shape changing elements ("wiring") 140 can be operable to change shape in response to an external stimulus. This change of shape effectively reduces the circumference of the wrap encircling the user, thereby applying pressure or a compressive force 170 to the user. In some embodiments, the wiring 140 is an element configured to change length, and more particularly to reduce its length in response to the stimulus. Wiring 140 can be one or more wires formed of a "shape memory" material or alloy that shrinks when a current is applied to the wire, and that returns to its original "memory" configuration when the current is removed or changed. In some embodiments, wiring 140 can include a wire formed of a "memory" material that changes length upon application of an electrical signal and then returns to its original length when the signal is terminated. Thus, the wiring activated and deactivated to create varying amounts of compressive forces on a user. The memory material can be a memory metal such as Nitinol. In other embodiments, electroactive polymers (EAP) can also be used in place of the Nitinol wires. EAPs are polymers that can exhibit a change in size and/or shape when stimulated by an electric field.

In some embodiments, the wiring 140 can extend through all or a substantial entirety of the length of a wrap. For example, a wrap 150 of second appliance 112 includes a first wire 160 that has been arranged to loop back-and-forth once along the wrap 150 (i.e., is doubled), forming an overall shape similar to an ellipse or rectangle. As will be discussed in greater detail below, the spacing between the looped sides of the first wire 160 is variable along the length of the wrap (see FIG. 2). In addition, because the wrap as worn is disposed in a doubled-layer (see FIGS. 3-7) the first wire 160 includes an outer segment 162 (solid lines) disposed further away from the user's skin and an inner segment 164 (dotted lines) disposed nearer to the user's skin. This wiring pattern enables the compression appliance to deliver four separate lines, pathways, or regions of compressive stimulation that rely on only a single, continuous length of wire, significantly reducing the amount of energy needed to power the compressive actions.

Figure 2:
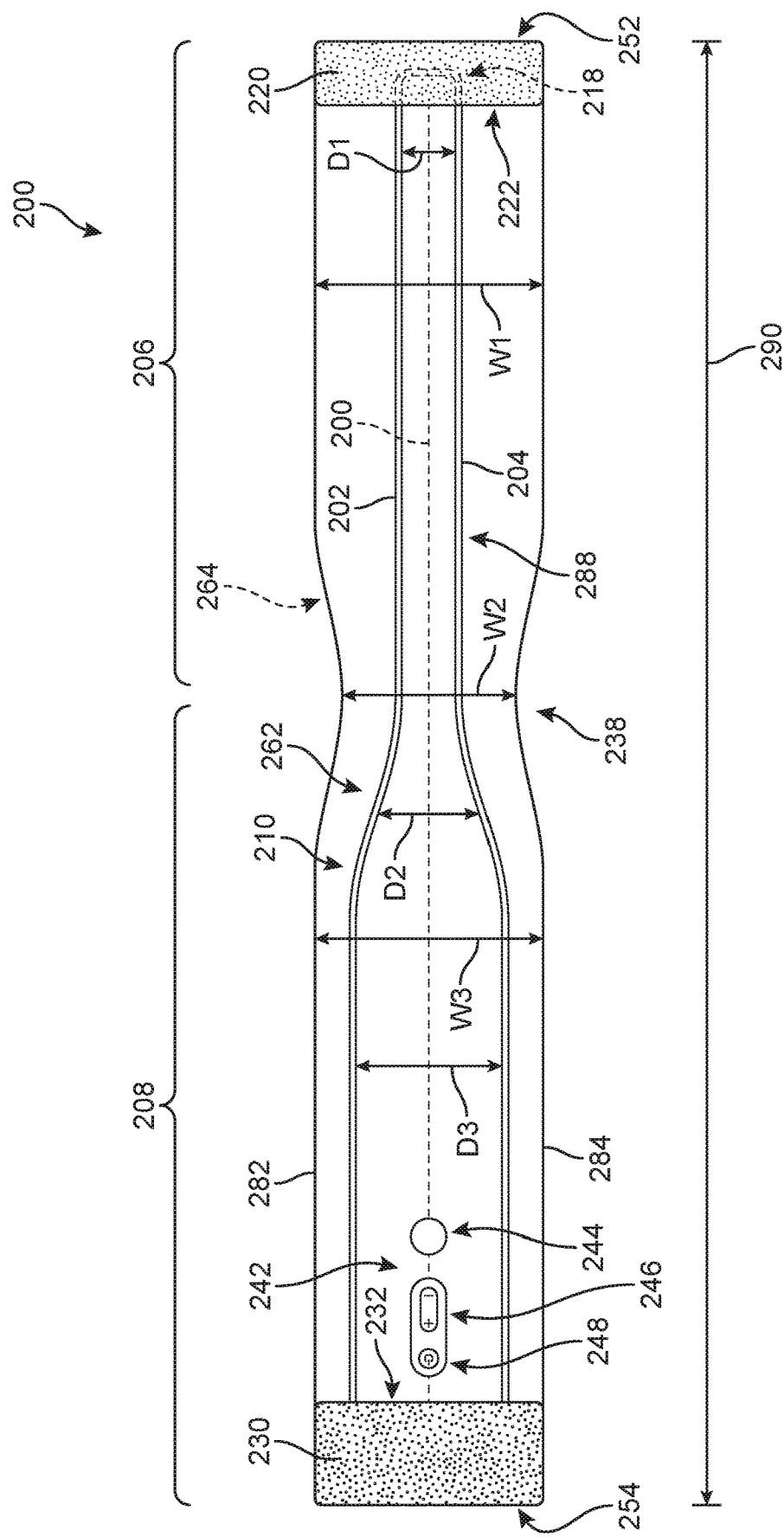
FIG. 2 is a schematic top-down view of an embodiment of a compression appliance.

For purposes of clarity, FIG. 2 presents a top-down view of an outwardly-facing surface side ("outward side") 262 of a compressive appliance 200. For reference, opposite inwardly-facing surface side ("inward side") 264 is designed to face toward the user's skin, while outward side 262 is designed to face away from the user's skin. As shown in FIG. 2, compressive appliance 200 can include a plurality of components, including an elongated wrap portion ("wrap") 210, a control interface 242, two end tab portions (a first end portion 220 and a second end portion 230), and wiring 288 embedded within the wrap 210 and the end portions.

While the compressive appliance 200 may be understood to extend fully across with a length 290 between a first end 252 and a second end 254, the wrap 210 itself only extends longitudinally between a first edge 222 and a second edge 232, where the first edge 222 borders the first end portion 220 and the second edge 232 borders the second end portion 230. The wrap 210 also extends in a lateral direction between an upper edge 282 and a lower edge 284. In addition, one or both end portions 220 and 230 can include one or more fastening mechanisms configured to secure the compressive appliance 200 once it has been wrapped around a body part (see FIG. 7 and FIGS. 10A and 10B).

The wrap 210 further includes a wiring arrangement in which a single wire extends from the electronic assembly housed primarily within second end portion 230. The wiring extends across the length of the wrap 210 and loops back within the first end portion 220 itself (e.g., see a loop terminus 280 indicated by dotted line), or elsewhere within the wrap 210, such that the wiring 288 can be understood to be doubled, forming two distinct pathways across the length of the wrap 210. As noted earlier, because the nitinol wires feature a limited coefficient of contraction, the repeated looping multiplies the compressive force and offers compression benefits similar to or greater than those experienced by wraps in which additional wiring lengths are integrated into the length of the wrap.

As shown in FIG. 2, an upper wire segment 202 of the wiring 288 runs along the upper region (i.e., relative to a midline 298) of the wrap 210, and a lower wire segment 204 of the wiring 288 runs along the lower region (i.e., relative to the midline 298) of the wrap 210. While the two segments are identified separately for purposes of reference, it should be understood that together they comprise a single (continuous) wire element. In some embodiments, the upper wire segment 202 and lower wire segment 204 are arrange symmetrically about the midline 298 (i.e., mirror-image). In other words, as a general matter, the spacing between the upper wire segment 202 and the midline 298 is substantially equal to the spacing between the lower wire segment 204 and the midline 298, allowing for a more even compressive distribution across the wrap.

In addition, to better appreciate some of the benefits provided by the compressive appliance 200, the wrap 210 has been demarcated into two zones, including a first zone 206 and a second zone 208, where the first zone 206 refers to the portion of the wrap 210 designed to initially wrap around a body part in a first spiral or circuit, and the second zone 208 refers to the portion of the wrap 210 designed to wrap subsequently around the first spiral (i.e., as an overlapping layer). In other embodiments, there may only be a single tab portion (i.e., second tab portion 230) such that the elongated wrap extends fully to one end of the compression appliance 200 that includes the first zone 206.

FIG. 2 also provides an overview of the relative dimensions of the compressive appliance 200 and relative arrangement of elements included in the compressive appliance 200. For example, the two zones can be understood to be further distinguishable by the spacing between the wire segments in the two zones. In FIG. 2, it can be observed that the first zone 206 generally has a lateral first width W1, and extends longitudinally from the first edge 222 to an optional neck region ("neck portion" 238) where the width of the wrap 210 can optionally narrow to a lateral second width W2. The second zone 208 extends from the neck portion 230 and has an average lateral third width W3. In this case, the first width W1 can be equal to or slightly smaller than the third width W3. In other embodiments, W1 may be significantly smaller than W3, such that at least a peripheral portion of the fabric of second zone will come into direct contact with the user's skin when the compression appliance 200 is fully wrapped. Outside of the neck portion 238, the two wire segments (upper wire segment 202 and lower wire segment 208) can be understood to be in a substantially parallel arrangement across a length of the wrap. Furthermore, second width W2 is smaller than both W1 and W2. In other embodiments, the width of the wrap 210 (e.g., W1, W2, W3) may be substantially uniform or equal across the length of the wrap 210, such that upper edge 282 and lower edge 284 remain substantially parallel.

Each of the two zones is associated with a particular wiring arrangement. In the first zone 206, a first distance D1 between the upper wire segment 202 and the lower wire segment 204 is generally uniform (such that the two wire segments are substantially parallel), until reaching the neck portion 238, when the spacing between the two wire segments begins to widen. For example, as the wrap 210 approaches and extends into second zone 208, the spacing between the two segments has grown to a second distance D2 greater than first distance D1. Thus, the neck portion 238 can also serve as a tangible indicator to a user that upon reaching the neck portion 238, a properly fitted compression appliance should have completed one loop around the user's body part.

Once the spacing grows to a third distance D3—larger than both D1 and D2—in the second zone 208, it may become substantially uniform or equal again. As a general matter, the first zone 206 may be understood to refer to the portion of the wrap 210 in which the spacing between the two wire segments is narrower and the second zone 208 refers to the portion of the wrap in which the spacing between the two wire segments is relatively wider. The actual distance can vary depending on the size of the specific compressive appliance 200, the body part for which it is designed, and the size of the person for whom it is targeted. In other words, if a body part is larger (e.g., a thigh), than the first zone and second zone will need to be longer to accommodate the larger circumference being covered, while smaller body parts (e.g., a wrist) will need to be shorter to accommodate the smaller circumference to be covered. This will also ensure that the first zone and the second zone overlap one another correctly once the compressive appliance is wrapped (i.e., avoiding the first zone overlapping with itself or the second zone overlapping with itself). Furthermore, because a second circuit will always be of a slightly larger circumference (due to the thickness added by the underlying wrap's first circuit corresponding to the first zone), the second zone can also be understood to have a longer length than the first zone.

In addition, in some embodiments, the compressive appliance 200 includes control interface 242 for interacting with the compression appliance 200. For example, control interface 242 can provide basic user controls accessibly embedded in the wrap. A user can interact with the basic user controls via the control interface 242 provided on the wrap and/or a mobile application (e.g., using a phone or other computing device) to instruct the microprocessor to implement a predetermined sequence and pattern of compression based on a selected compression profile and heat setting. The mobile application can be configured to provide substantially similar selectable options as those offered by the control interface 242 and connect to the compression appliance via a communication module of the compression appliance. For example, the electronic assembly can include a communication module that enables a wireless connection using Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. In many cases, the communication module is a wireless connection; however, wired connections may also be used. For example, the communication module may include a wired serial bus such as a universal serial bus or a parallel bus, among other connections.

Thus, although not depicted in the drawings, in different embodiments, a user can use the interface provided by a mobile application to change the compression settings. The application ("app") can offer a user interface that may be accessed via any user computing device configured for connection to a network. In different embodiments, the application can be configured to offer content via native controls presented via an interface. Throughout this application, an "interface" may be understood to refer to a mechanism for communicating content through a client application to an application user. In some examples, interfaces may include pop-up windows that may be presented to a user via native application user interfaces (UIs), controls, actuatable interfaces, interactive buttons or other objects that may be shown to a user through native application UIs, as well as mechanisms that are native to a particular application for presenting associated content with those native controls. In addition, the terms "actuation" or "actuation event" refers to an event (or specific sequence of events) associated with a particular input or use of an application via an interface, which can trigger a change in the display of the application. This can include selections or other user interactions with the application, such as a selection of an option offered via a native control, or a 'click', toggle, voice command, or other input actions (such as a mouse left-button or right-button click, a touchscreen tap, a selection of data, or other input types). Furthermore, a "native control" refers to a mechanism for communicating content through a client application to an application user. For example, native controls may include actuatable or selectable options or "buttons" that may be presented to a user via native application UIs, touch-screen access points, menus items, or other objects that may be shown to a user through native application UIs, segments of a larger interface, as well as mechanisms that are native to a particular application for presenting associated content with those native controls. The term "asset" refers to content that may be presented in association with a native control in a native application. As some non-limiting examples, an asset may include text in an actuatable pop-up window, audio associated with the interactive click of a button or other native application object, video associated with a teaching user interface, or other such information presentation.

In different embodiments, the control interface 242 can be disposed in a predetermined location along or accessible via an outwardly facing surface of the wrap disposed toward second end 254. The control interface 242 is electrically connected to the controller such that the controller can receive input from a user via the control interface 242 and transmit corresponding instructions to the relevant components of the electronic assembly (see FIG. 8). For example, the control interface 242 can include a power button 244, a function button 246, and a charge indicator 248. The power button 244 is used to turn the compression appliance on and off, while the charge indicator 248 can indicate a remaining charge in the power source. The function button 246 can be configured to select from a plurality of compression profiles and heat settings. In other words, the function button can be configured to instruct the microprocessor to implement a predetermined compression profile and/or heat setting. The function button 246 can be pressed once to select a first predetermined option, long pressed (e.g., longer than three seconds), and/or the function button can be pressed a plurality of times to cycle through additional compression profile and/or heat setting options. In other embodiments, the control interface 242 may include additional or alternate options for interacting with the appliance.

Figure 3:
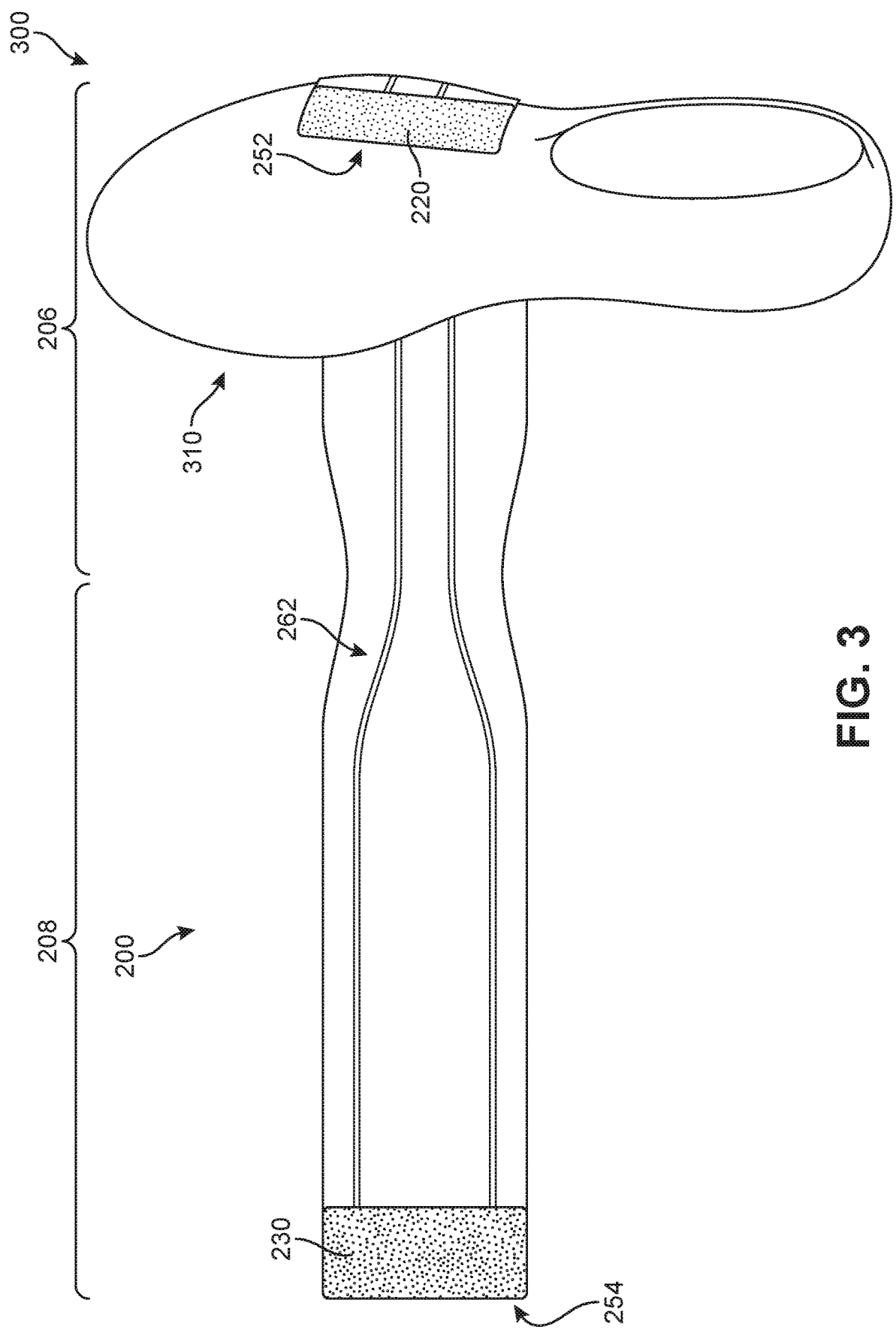
FIG. 3 is a top-down view of an embodiment of the compression appliance disposed adjacent to a foot in an initial wrapping stage.

Referring to FIGS. 3-7, a sequence of drawings illustrates one embodiment of a compression appliance system and method of applying or using such a system. In these drawings, the appliance will be shown as applied to a human foot. However, it should be understood that this use is presented as an example only, and the compression appliance can be readily applied to a wide range of other anatomical regions, including but not limited to regions legs, arms, torsos, waists, and necks. In the example of FIG. 3, in a first stage 300, the compressive appliance 200 is disposed and arranged in part beneath a foot 310. More specifically, first zone 206 of the compressive appliance 200 is positioned such that the first end 252 is disposed at the user's desired starting point, here on a lateral side portion of the foot 310 in the midfoot region, and first zone 206 continues along underneath foot 310 (e.g., inner surface 262 is pressed along or contacts the arch or sole of the foot), while second zone 208 terminating in second end 254 extends in a distal direction away from the foot. In other embodiments, the user may elect to begin the wrapping process in the opposite direction by rotation of the wrap approximately 180 degrees, such that the first end 252 is disposed along the medial side of the foot and the remainder of the wrap instead extends toward the lateral side. Furthermore, the starting point (location where first end 252 will be initially positioned) can vary widely around the foot (or other anatomical region) per the user's preferences. Thus, the specific descriptions of relative wrap location to the foot can vary from what is shown.

Figure 4:
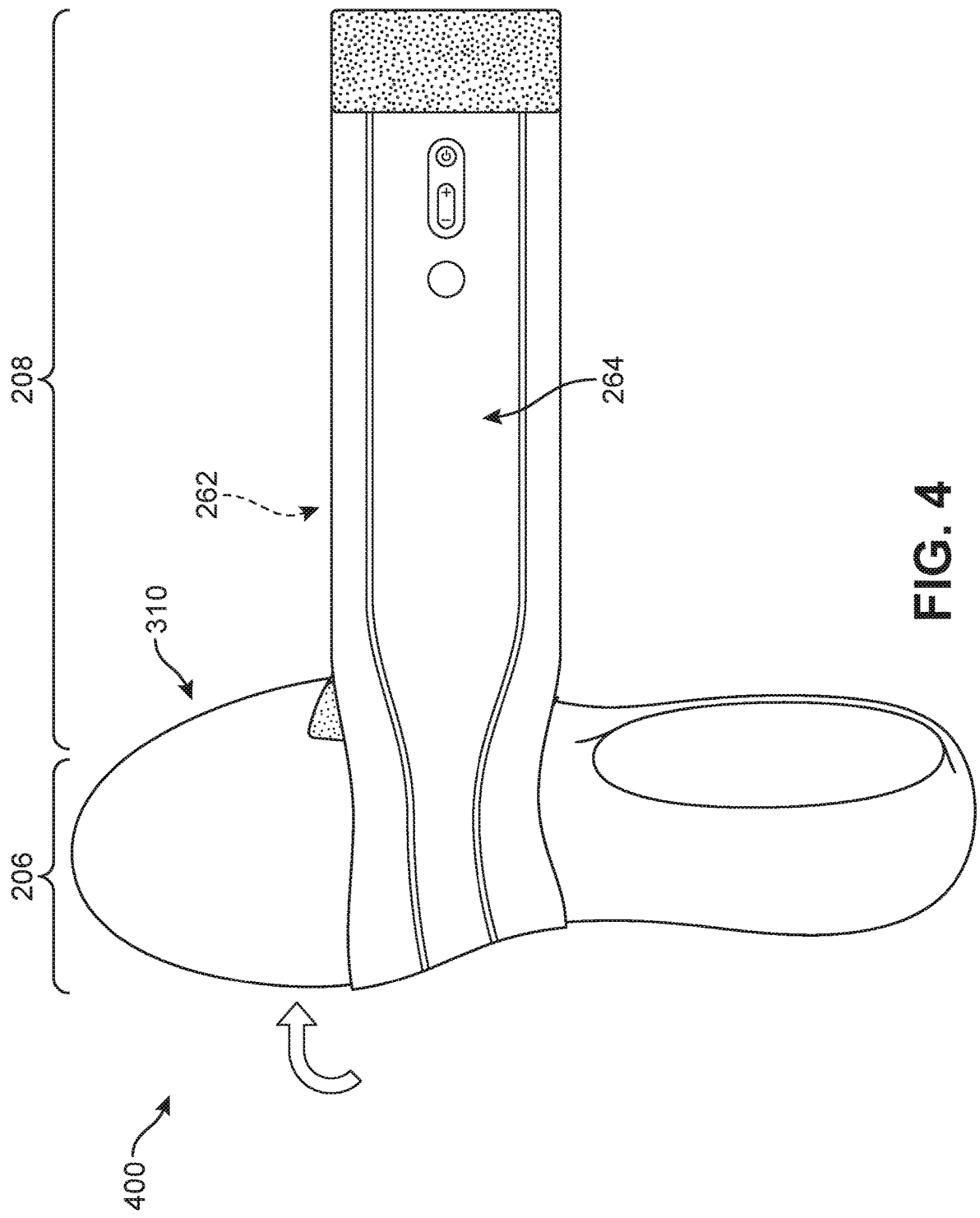
FIGS. 4 and 5 are a depiction of a wrapping stage of the compression appliance in which a first zone completes a circuit around the foot.

In FIG. 4, during a second stage 400, the first zone 206 is pulled upwards toward the foot 310 and its inner surface 262 lain against the upper part of the foot from the medial side toward the lateral side, until the first end 252 is in contact with a portion of the wrap. This completes a first full circuit of the foot, which also coincides with the full application of first zone 206 around the foot. In other words, any subsequent wrapping of the foot will now be provided by the second zone 208 of the wrap. Thus, each zone of the compression appliance may be understood to be configured to serve or correspond to a loop around the user's body part. In this case, the first zone 206 corresponds to a first loop of the wrap, while the second zone 208 will correspond to a second loop of the wrap. Additional zones (see FIG. 9A) could also provide additional full loops of material.

Figure 5:
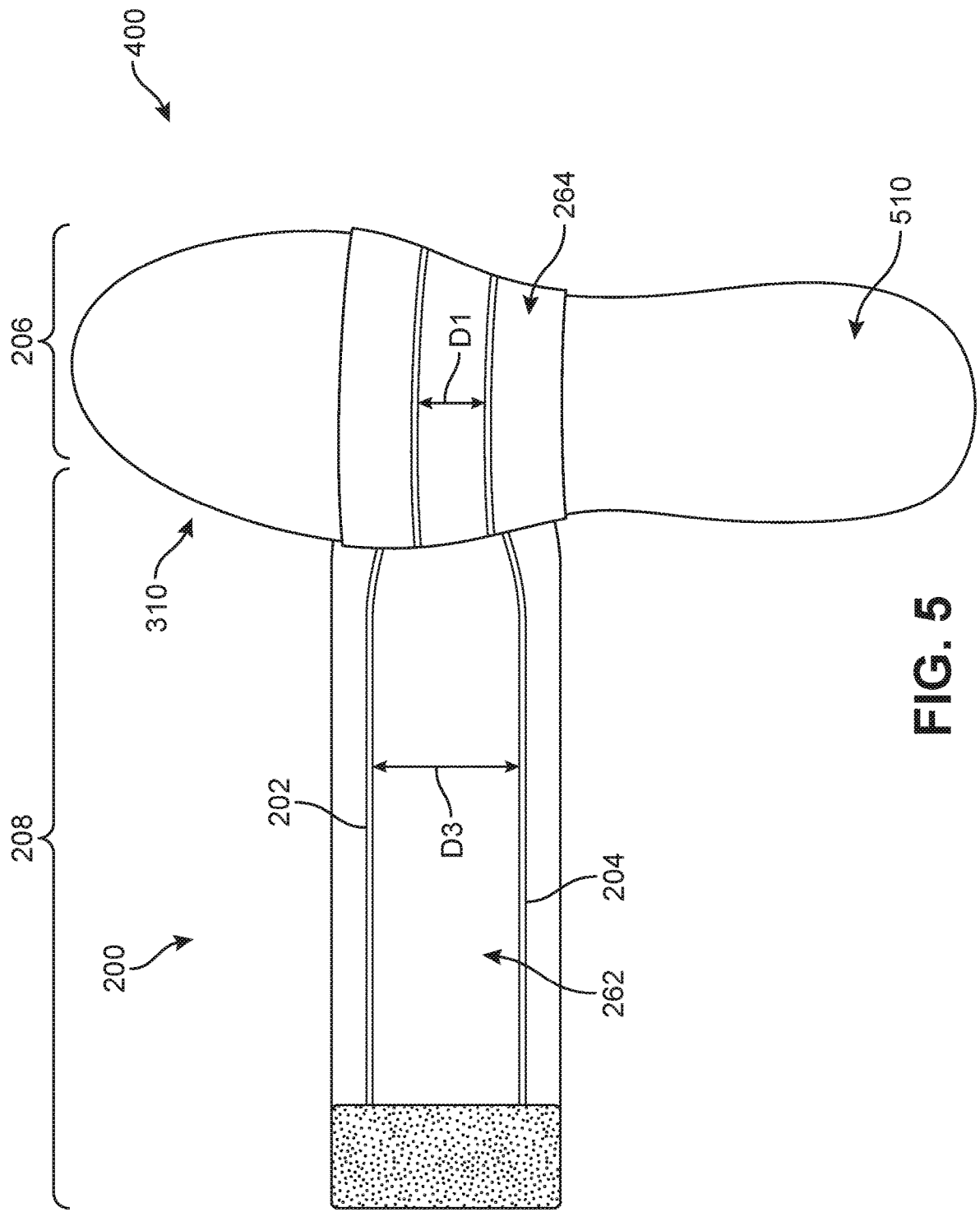

Referring next to FIG. 5, for purposes of clarity, the second stage 400 is depicted such that the foot 310 is now being viewed from the bottom (i.e., sole 510). The outer surface 264 of first zone 206 faces outward as first zone 206 has been wrapped around foot 310. In addition, inner surface 262 of second zone 208 is presented in a yet-unwrapped condition. The view of FIG. 5 can allow the reader to more clearly note the difference in spacing (~D1) within the first zone 206 between the upper wire segment 202 and the lower wire segment 204 relative to the spacing (~D3) between the upper wire segment 202 and lower wire segment 204 within the second zone 208. It is apparent in FIG. 6 that as the second zone 208 begins to be wrapped around the foot in a third stage 600, the inner surface 262 of second zone 208 will be placed in contact with the outer surface 264 of the first zone 206. During the subsequent second circuit around the foot 310, the two surfaces will be disposed or pressed against one another. However, due to the variation in spacing in the two zones, the upper wire segment 202 and the lower wire segment 204 in the second zone 208 do not make contact with the previous lengths of the upper wire segment 202 and lower wire segment 204 in the first zone 206. In other words, the wiring extending through second zone 208 remains offset from the wiring extending through first zone 206 when the two zones overlap.

Figure 7:
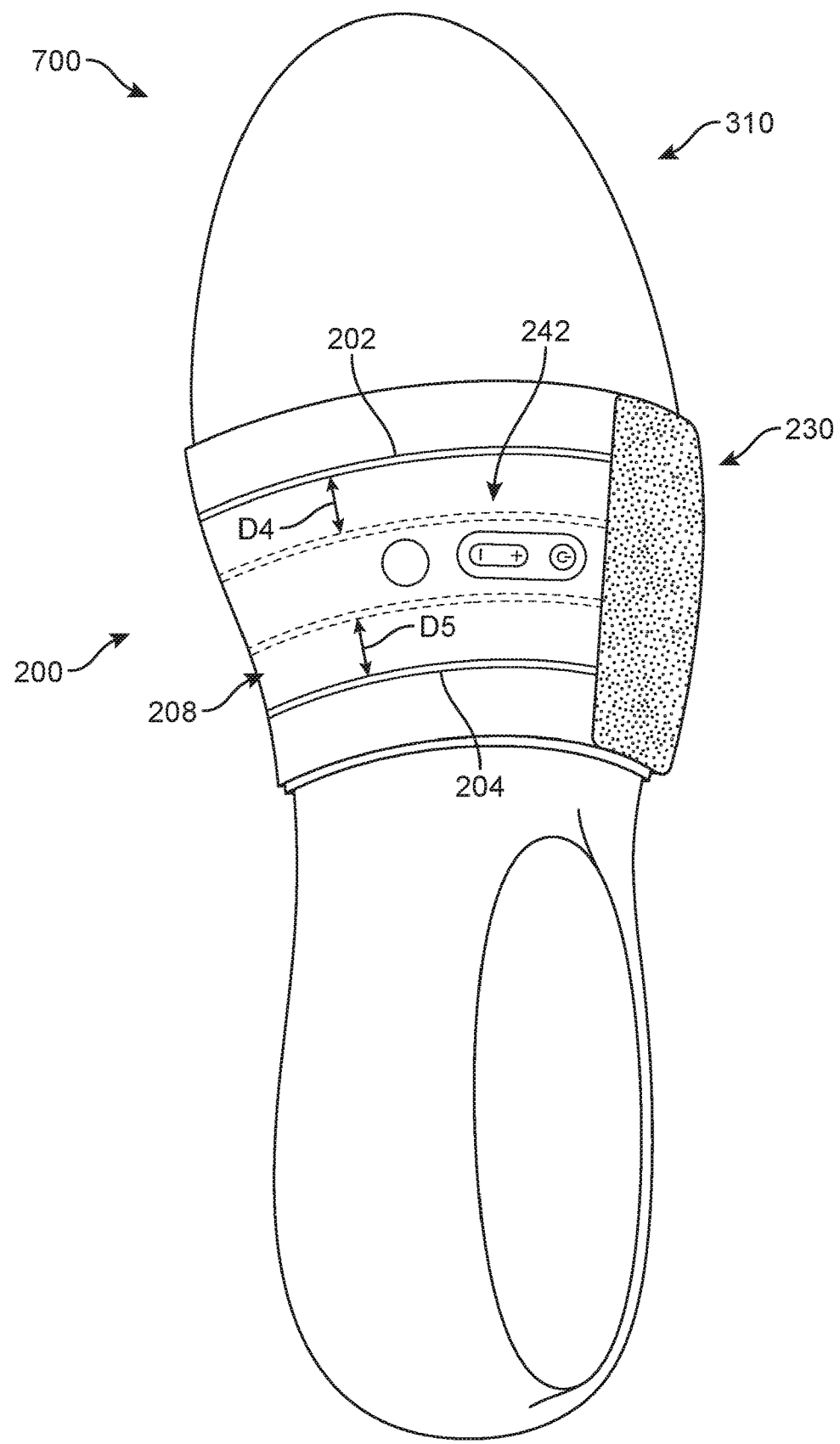

Finally, in FIG. 7, the wrapping of the compression appliance 200 around foot 310 is completed in a fourth stage 700. For purposes of comparison, the wiring extending through first zone 206 (more proximate to the foot itself) is depicted in dotted line, while the wiring extending through second zone 208 is depicted in solid line. FIG. 7 more clearly presents the manner in which the compression appliance 200 can provide two overlapping layers around the foot 310 in an axial direction, with two segments of wiring extending throughout its length, yet the wiring segments remain separate or spaced apart from one another. For example, the upper wire segment 202 in the first zone 206 is spaced apart from the upper wire segment 202 in the second zone 208 by a distance D4, and the lower wire segment 204 in the first zone 206 is spaced apart from the lower wire segment 204 in the second zone 208 by a distance D5. This permits the compression appliance 200 to provide a broad distribution of compressive force across a substantial width of the wrap by passing current through four distinct paths of wiring.

Upon completion of this type of spiral wrapping process, the fastening mechanism associated with second end portion 230 can be used to secure the compression appliance in place. In some embodiments, the inner-facing surface of the second end portion 230 can include a first fastening material that is configured to grip, hook, or otherwise removably adhere to a second fastening material comprising an outer-facing surface of the second zone. For example, a hook and loop fastener material may be used to keep the wrap closed around the joint or other area of the body. In other embodiments, any type of releasable fastener may be incorporated into the wrap, where one component of the fastener is disposed along the second end portion 230 to provide an apparent seam between the overlapping layers of textile. Because the wrap is constructed at least in part from an elastic material, it is resilient and durable and able to withstand an amount of strain. Thus, when the second end portion 230 is pulled tight across prior to fastening, the wrap readily withstands the force. For example, the end of the wrap, where the fastener may be configured to attach to some portion of the outer surface of the second zone. The fastener mechanism—which may refer collectively to a group of fastening elements—may comprise any conventional reusable means for fastening such as, but not limited to, hook and loop fasteners, buttons, snaps, clamps, clips, latches, pins, ties, adhesive, magnets, etc. that will have a corresponding "receiving" portion in the second zone configured to connect or latch and secure the end of the wrap. For example, if a magnet is used in the second end portion 230, a magnetic material may be distributed through the textile to allow for the two segments to releasably lock together.

Figure 8:
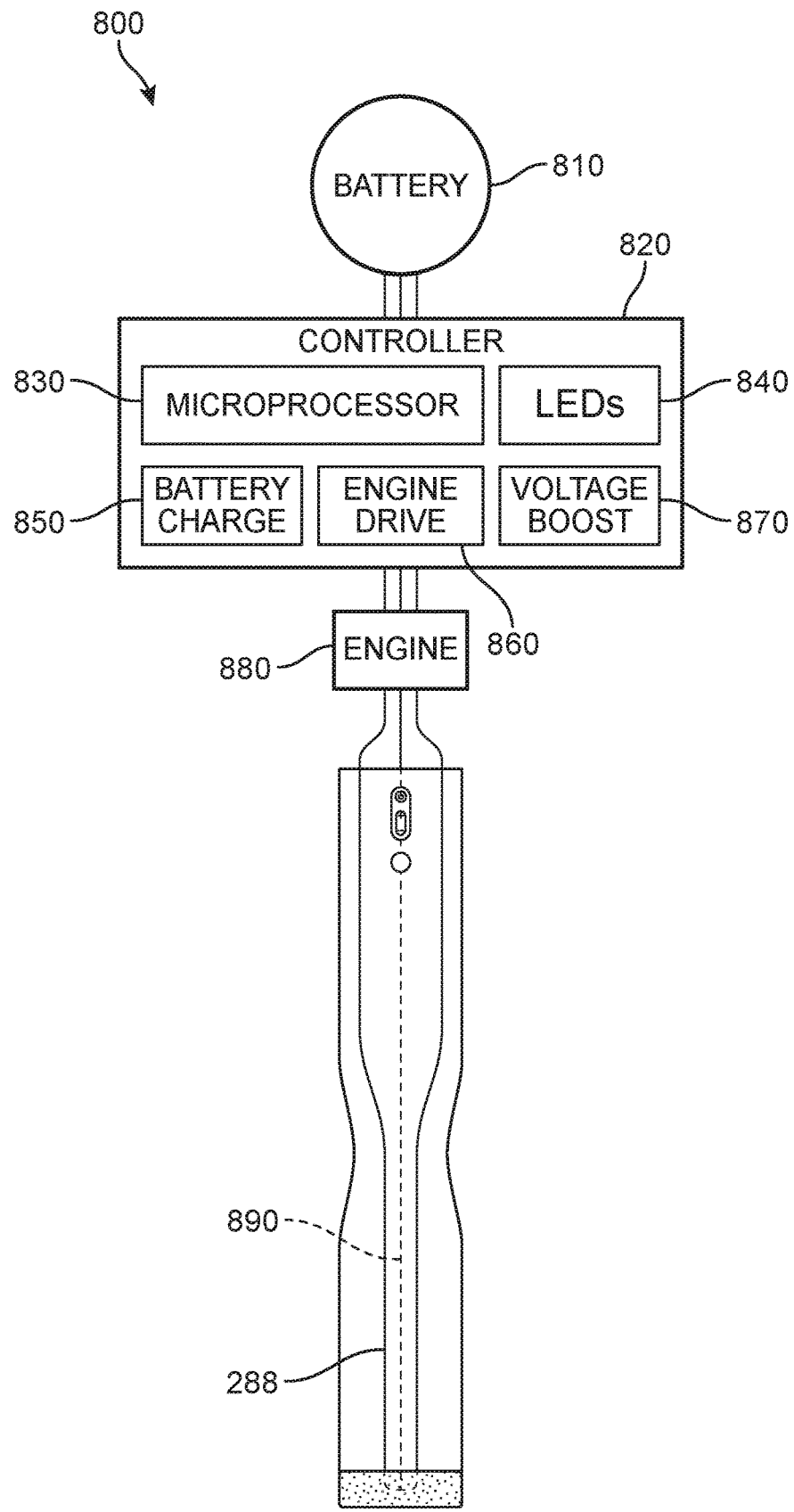
FIG. 8 is a top-down view of the compression appliance that includes a schematic view of an integrated electronic assembly, according to an embodiment.

Referring now to FIG. 8, an embodiment of a hardware block diagram of an electronic assembly 800 as included in the compression appliance 200 is presented. As shown in FIG. 8, the electronic assembly 800 can include or be powered by a battery 810. The electronic assembly further includes a controller 820, a wiring engine 880, wiring 288, and a ground 890. The controller 820 can further include or be connected to a microprocessor 830, a battery charge 850, an engine drive 860, LEDs 840, and/or a voltage boost 870. In some embodiments, the electronic assembly 800 or portions thereof can be disposed on at least one of a flexible printed circuit board (PCB) or FR4.

As noted earlier, wiring 288 can comprise a shape memory alloy, such as Nitinol, which includes an alloy of nickel and titanium that, when in a shape-memory state, can undergo a molecular reconfiguration in response to a predetermined temperature change. The SMA wiring can contract in response to being heated above a predetermined transformation temperature corresponding to the specific material comprising wiring 288 and return to its original state when cooled. The transformation temperature is a predetermined temperature based on the characteristics of the SMA wire (e.g., shape, size, composition, etc.). Under expected operating conditions, Nitinol can be subjected to millions of cycles. Although Nitinol exhibits superior characteristics over other metals, stress in the form of overheating or high forces can have a negative impact on the life of the wire, and so other material compositions may be used.

As arranged in compression appliance 200, the single wire can provide a plurality of channels of compressive force. The looped wire can be part of or be bridged or connected at the wiring engine 880, and the wiring engine 800 is further connected to the controller 820. The engine drive 860 can energize and de-energize the wire within the wiring engine 880 based on firmware programmed into the microprocessor 830. The energizing and de-energizing causes the wiring 288 to contract (e.g., shorten) and relax (e.g., elongate), thus providing the active compressions when the compression appliance 200 is applied to a user's body. In addition, the microprocessor 830 can control a sequence and magnitude of a current applied to the upper wire segment and lower wire segment simultaneously or independently. In one embodiment, the microprocessor 830 may be preprogrammed with one or more particular compression sequences for a particular user. The compression appliance 200 may be provided in varying dimensions that may be distinguished based on a length of the wrap and corresponding wire. A compression sequence may include an infinite or continuous rolling in which the wrap is successively compressed around a user's body similar to a peristaltic movement, a step-wise sequence in which the wrap is compressed and held for a period, or even a random sequence. Other compression protocols may be preprogrammed into the microprocessor 830 that can be selected by the user as desired via interface.

In some embodiments, the controller 820 includes a Parallax microcontroller, such as Parallax microcontroller Part No. BS2-IC. In other embodiments, microcontrollers such as Arduino, Tessel, LaunchPad, Picaxe, Wiring, Netduino, TinyDuino, DigiSpark, Raspberry Pi, BeagleBone, pcDuino, Gizmo, FPGAs, as well as boards configured with GSM cellular, wi-fi, Bluetooth Low Energy, mesh networking, and other wireless capabilities, may be used.

When the wiring is activated, the microprocessor 820 can direct current to the specific wire or wires, thereby causing one or both segments of the wire to contract or shrink, which reduces the effective diameter of the wire. This reduction in diameter translates to an application of pressure of material that is in contact with the user. When the current is removed or changed, the "memory" feature of the wiring allows it to return to a deactivated or neutral condition, thereby removing pressure from the associated wrap. In addition, the user's body can act as a spring to assist in returning the memory wire(s) to the neutral phase.

Both ends of the wire can be connected to the wiring engine 880. Generally, the wiring engine 880 can provide active compressions and therapeutic heat. More specifically, the wiring engine 880 can be configured to provide electrical current to each segment of wiring 288 via the instruction of the microprocessor 820. Electrical current can be applied to the wiring 288 at contact mounts to heat the wires beyond a predetermined transition temperature and to cause the wiring 288 to change length or contract, thereby applying compression. This electric current can be applied in specific patterns to create predetermined compression profiles and heat settings. Additionally, the wiring 288 can be encapsulated in Teflon tape that provides electrical, moisture, and thermal insulation to prevent damage due to the heating of the wiring 288. The insulation provided via the Teflon tape can be a first mechanism to control heat created from the electrical current being applied to the wiring 288. The heat can be controlled so the user gets the therapeutic benefits provided by the heat while still maintaining a temperature that meets various medical standards. In different embodiments, the wiring engine 880, and associated wiring 288, can be pretensioned to enable the wire segments to return to their original position quickly once cooled. The pre-tensioning can be achieved via, for example, a Boa lace and Boa dial incorporated in the compression appliance.

In addition, as noted earlier, electronic assembly 800 includes a battery 810 that provides a power supply to the unit. In some embodiments, the power supply can be a lithium ion battery or other rechargeable battery that can be recharged via battery charge 850. Non-limiting examples of such a battery include button cell batteries and hearing aid batteries, though other small power sources may be used. In some embodiments, the power source and electronic assembly is embedded in a housing contained in the second end portion 230. In some embodiments, the housing and/or second end portion 230 may include a removable cover to provide a user access to components in case one or more components needs to be replaced.

Thus, while in conventional systems the use of a single SMA wire around a body part, such as a thigh, does not provide sufficient compression for most purposes, by incorporating a double layered wrap in which two zones of the wire overlap one another, the compression force is able to be distributed over a larger area while avoiding the single wire "garroting" effect. Furthermore, reducing the number of SMA wires embedded in the appliance to a single wire allows compression forces to be provided in a highly energy efficient manner without the need for amplification. In addition, heat transmission and build-up between the wire segments during actuation can be reduced by ensuring there is no contact between the various wire segments. Furthermore, the battery type required for a single wire can be smaller and/or of a lower power rating relative to compression appliances using multiple wires. For example, it is contemplated that a power source in the range of 1-40 watts can be required to produce effective results for large scale compression. This power requirement can be satisfied by a battery offering lower 30-100 mAh capacity range, whether by the use of on-board high-energy batteries, such as lithium polymer batteries, or by the use of an electrical adapter/transformer connected to a separate electrical source.

Figure 9A:
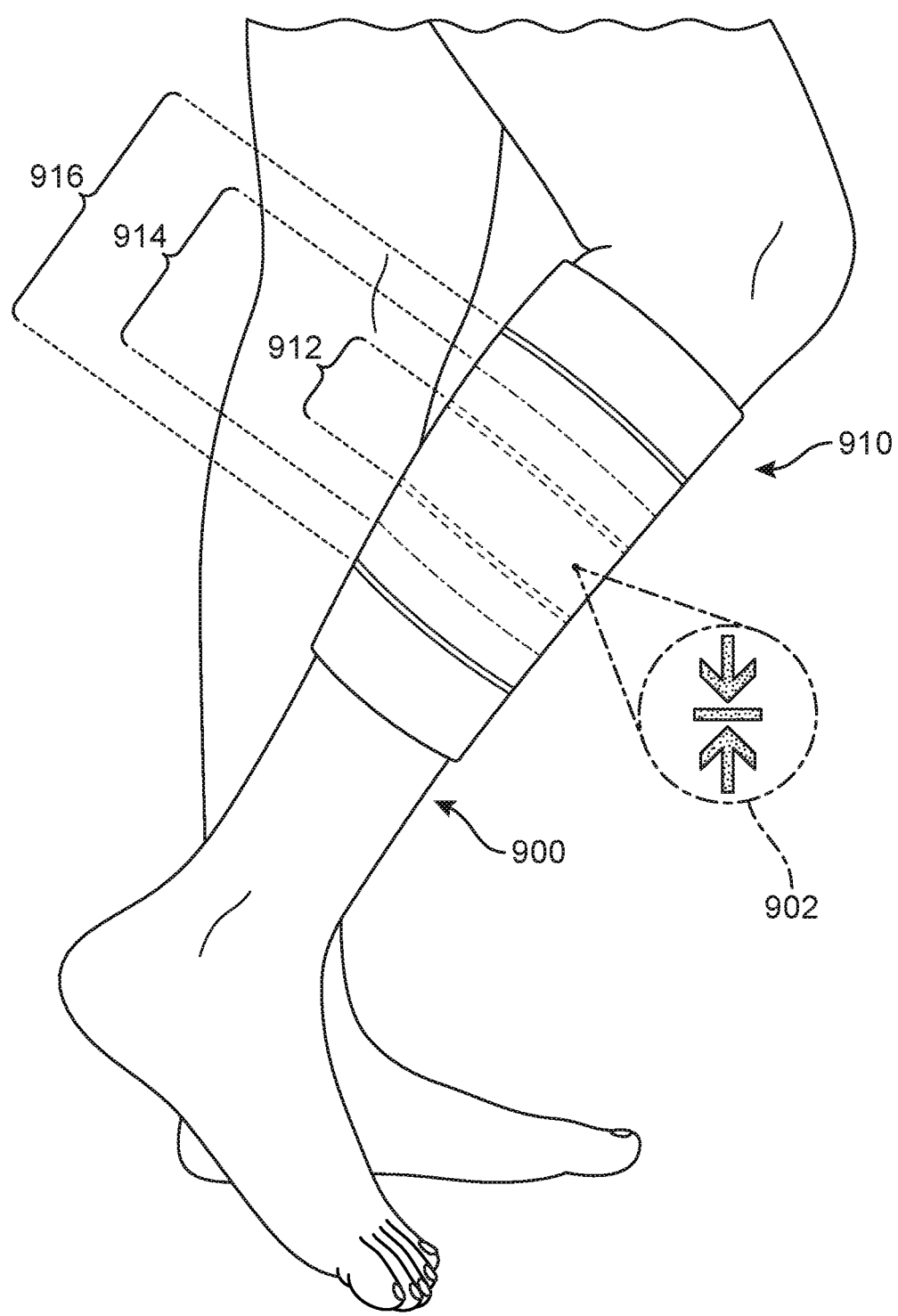
FIG. 9A is an alternate embodiment of a compression appliance which is wrapped around the ankle of a user.
Figure 9B:
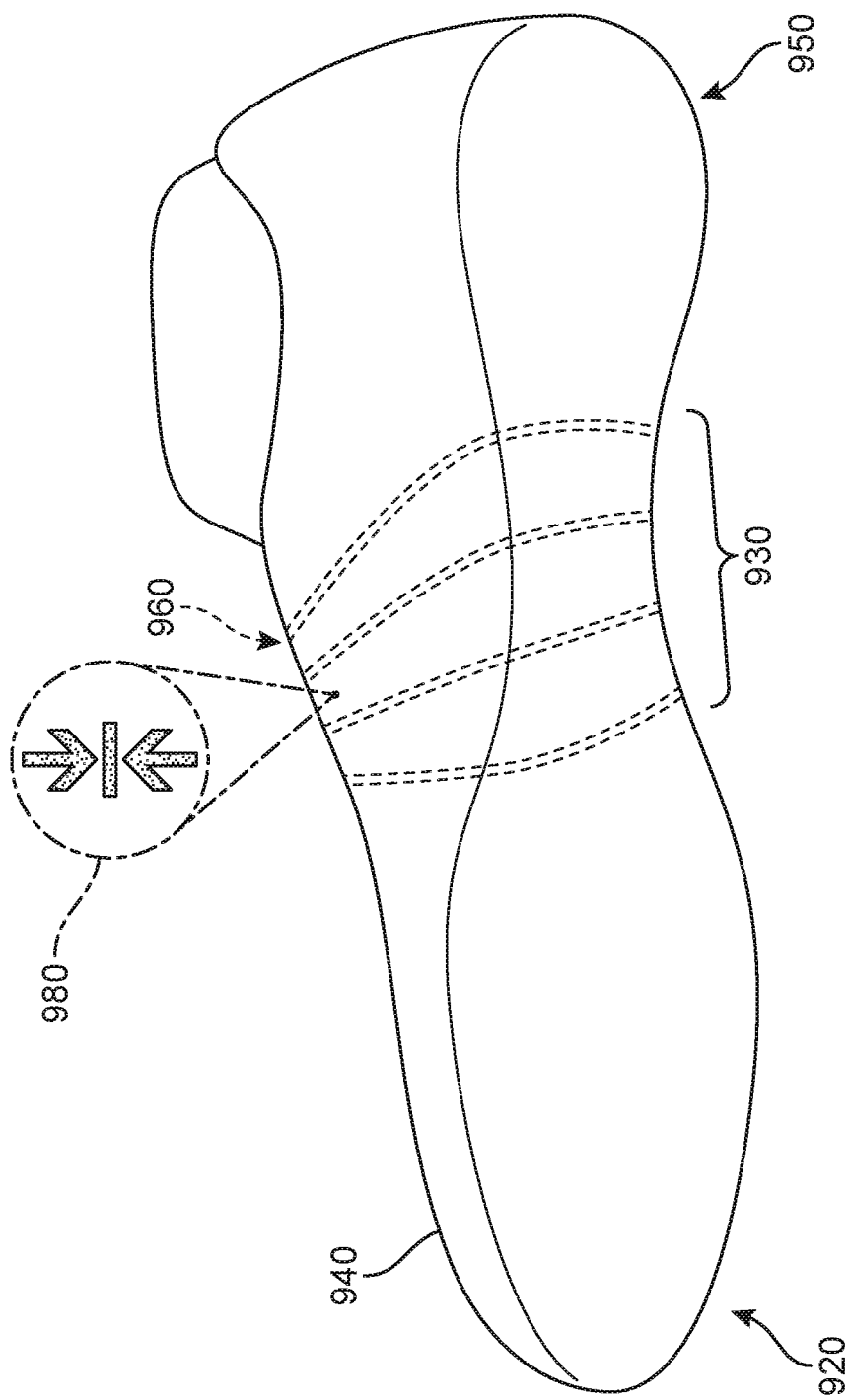
FIG. 9B is an alternate embodiment of a compression appliance that has been incorporated into a closed-toed article of footwear.
Figure 9C:
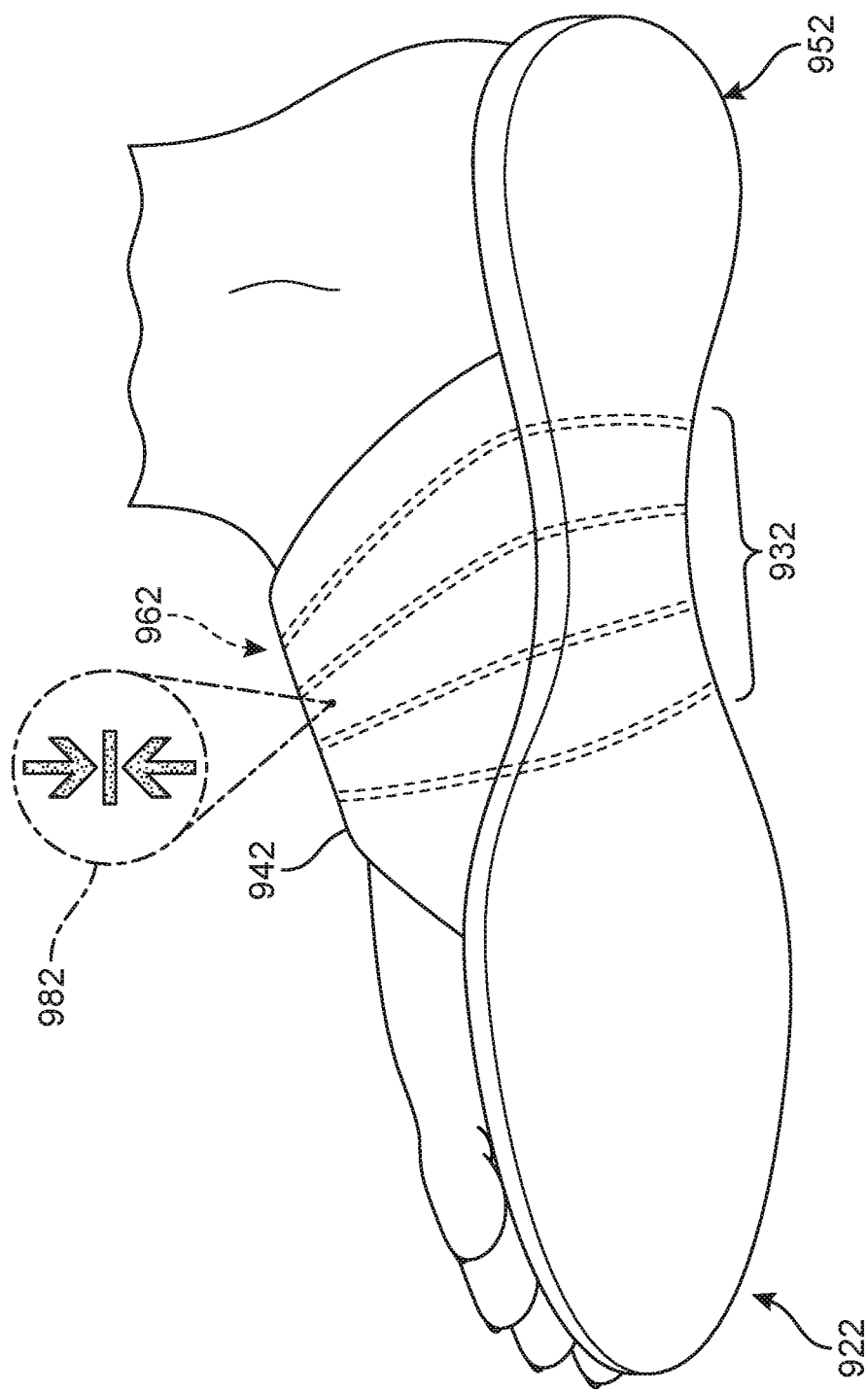
FIG. 9C is an alternate embodiment of a compression appliance that has been incorporated into an open-toed article of footwear.

For purposes of illustration, three alternate embodiments of the proposed compression appliance system are presented with reference to FIGS. 9A-9C. In FIG. 9A, a second compression appliance ("second appliance") 910 is depicted. In this example, the second appliance 910 can be understood to include a wider wrap that can extend from below the knee to the ankle area of a leg 900. In order to provide a compressive force 902 over a larger surface area while still using the single wiring arrangement, the wrap may include multiple zones in which the upper wire segment and lower wire segment (segment pairs) are spaced apart by increasingly greater distances. In this case, the wrap includes three zones; the first zone is disposed closest to the skin of the leg and includes innermost wiring segment pair 912, a third zone disposed most distal from the skin of the leg, presents the exterior surface of the installed wrap, and includes an outermost wiring segment pair 916, and a second zone disposed or interleaved between the first zone and the second zone that includes an intermediate wiring segment pair 914. In other embodiments, the second appliance 910 can be limited to two zones as described earlier, and include a first zone and second zone that are both greater in length to accommodate the thicker diameter of the calf relative to a foot. Compression appliances can be offered which incorporate a wide variety of such differences of shape and size to allow users of various body types and needs to find a suitable match.

In FIGS. 9B and 9C, two alternate embodiments in which a compression appliance has been integrated into an article of footwear ("footwear") are presented. For purposes of this application, articles of footwear can include, but are not limited to, hiking boots, soccer shoes, football shoes, sneakers, running shoes, cross-training shoes, rugby shoes, basketball shoes, baseball shoes as well as other kinds of shoes. Moreover, in some embodiments, components may be configured for various kinds of non-sports-related footwear, including, but not limited to, slippers, sandals, including "slide-on" sandals, high-heeled footwear, loafers as well as any other kinds of footwear. Articles of apparel include, but are not limited to, socks, pants, shorts, shirts, sweaters, undergarments, hats, gloves, as well as other kinds of garments. Accessories include scarves, bags, purses, backpacks, as well as other accessories. Equipment may include various kinds of sporting equipment including, but not limited to, bats, balls, various sporting gloves (e.g., baseball mitts, football gloves, ski gloves, etc.), golf clubs, as well as other kinds of sporting equipment.

Articles of footwear often include two primary elements, an upper and a sole structure, the upper being configured to contain or at least partially surround the foot, and the sole structure being configured to contact the ground. The upper is often formed from a plurality of material elements (for example, textiles, polymer sheets, foam layers, leather, and/or synthetic leather) that are stitched and/or adhesively bonded together to form an interior cavity for receiving a foot of a wearer. The "inner side" or "inside" of an element refers to the face of that element that is (or will be) oriented toward the internal cavity in a completed article of footwear. The "outer side," "outside," or "exterior" of an element refers to the face of that element that is (or will be) oriented away from the internal cavity in the completed article of footwear. In some cases, the inner side of an element may have other elements between that inner side and the interior in the completed article of footwear, as will be described below. Similarly, an outer side of an element may have other elements between that outer side and the space external to the completed article of footwear. Further, the terms "inward" and "inwardly" shall refer to the direction toward the interior of the article of footwear, and the terms "outward" and "outwardly" shall refer to the direction toward the exterior of article of footwear.

As a general matter, the upper provides a covering for the wearer's foot that comfortably receives and securely positions the foot with respect to the sole structure. An upper may be of a variety of styles depending on factors such as desired use and required ankle mobility. For example, an athletic shoe with an upper having a "low-top" configuration extending below the ankle that is shaped to provide high mobility for an ankle. An upper could be configured as a "high-top" upper extending above the wearer's ankle for basketball or other activities, or as a "mid-top" configuration extending to about the wearer's ankle. Furthermore, an upper may also include non-athletic shoes, such as dress shoes, loafers, sandals, and work boots. The sole structure is positioned between a foot of a wearer and the ground, and may incorporate various component elements. For example, sole structure may include one or more of inner sole components or "insoles," a middle sole element or "midsole," and an outer sole element or "outsole." An insole may take the form of a sockliner adjacent the wearer's foot to provide a comfortable contact surface for the wearer's foot. It will be understood that an insole may be optional. Further, a midsole may directly serve as a cushion and support for the foot. In addition, an outsole may be configured to contact the ground surface.

In FIG. 9B, an alternate embodiment in which a third compression appliance ("third appliance") 930 has been integrated into an article of footwear ("footwear") 920 such as a sneaker or other closed-toe shoe is depicted. As shown in FIG. 9B, a compression system can be provided in footwear whereby the 'wrap' portion of the appliance is replaced or otherwise incorporated directly into portions of interior materials comprising an upper 940 and sole 950 to provide a compressive force 980. For example, a single wire 960, comprising shape memory alloy materials, may be wrapped around in a loop in two or more circuits to offer the same or similar functionality provided by the compression appliances described earlier. The wire 960 can extend around a region of the shoe (e.g., forefoot, midfoot, hindfoot) and its looping terminus may be anchored within the footwear itself. Thus, a single wire element extends in multiple circuits around the shoe, integrated within both the upper and sole structure. The single wire element—being doubled—provides at least four spaced apart wire segments that encircle the article of footwear. When the wire 960 is actuated, all four pathways corresponding to the spaced apart wire segments are configured to constrict around a user's foot.

In FIG. 9C, an alternate embodiment in which a fourth compression appliance ("fourth appliance") 932 has been integrated into an article of footwear ("footwear") 922 such as a sandal is depicted. As shown in FIG. 9C, a compression system can be provided in footwear whereby the 'wrap' portion of the appliance is replaced or otherwise incorporated directly into portions of interior materials comprising an upper covering 942 and sole 952 to provide a compressive force 982. For example, a single wire 962, comprising shape memory alloy materials, may be wrapped around in a loop in two or more circuits to offer the same or similar functionality provided by the compression appliances described earlier. The wire 962 can extend around the midfoot of a person's foot when the foot is inserted or slid into the sandal, where the loop circuits formed by the wraparound wire 962 are embedded in the upper covering 942. Thus, a single wire element extends in multiple circuits around the sandal, integrated within both the upper and sole structure. The single wire element—being doubled—provides at least four spaced apart wire segments that encircle the article of footwear. When the wire 962 is actuated, all four pathways corresponding to the spaced apart wire segments are configured to constrict around a user's foot. Such a device can be useful for those who are seeking a more casual on-off appliance experience, and allows for a simple, comfortable feel that provides a powerful compression functionality.

In these two examples, the electronic assembly can also be disposed at least partially within the footwear components, for example within the sole, tongue, and/or upper or upper covering. The systems embedded in footwear as shown in the examples of FIGS. 9A and 9B can provide a seamless mobility experience. The footwear can further include a port configured to connect a charging station to the power supply. Such an arrangement can allow users to enjoy the benefits of the compression appliance at any time without the inconvenience of removing their footwear or worrying that activity or exposure to the elements might cause damage to the appliance, for the system is protected by the outer material of the footwear.

Figure 10A:
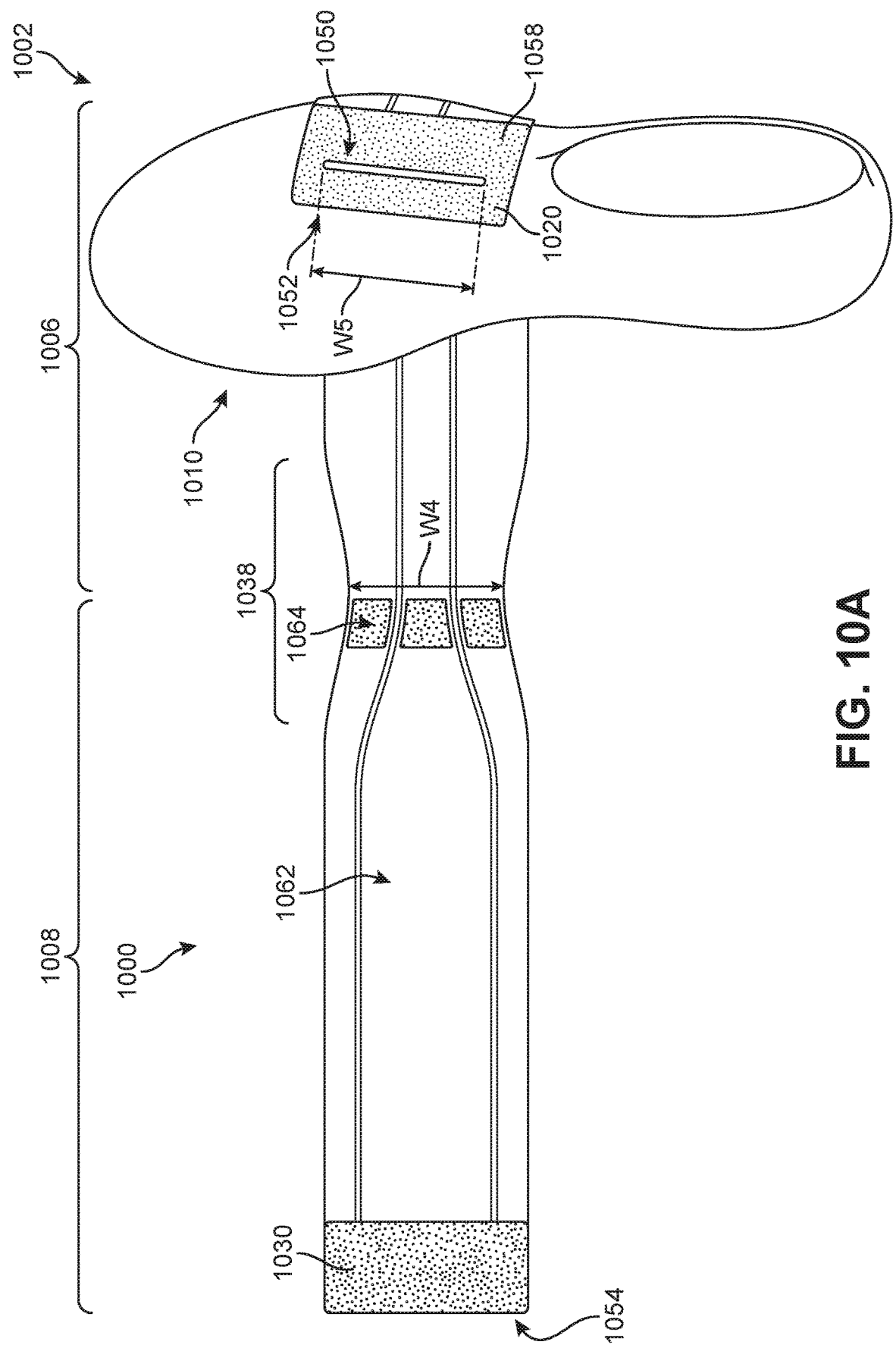
FIGS. 10A and 10B depict an embodiment of a compression appliance including a slot securing mechanism.
Figure 10B:
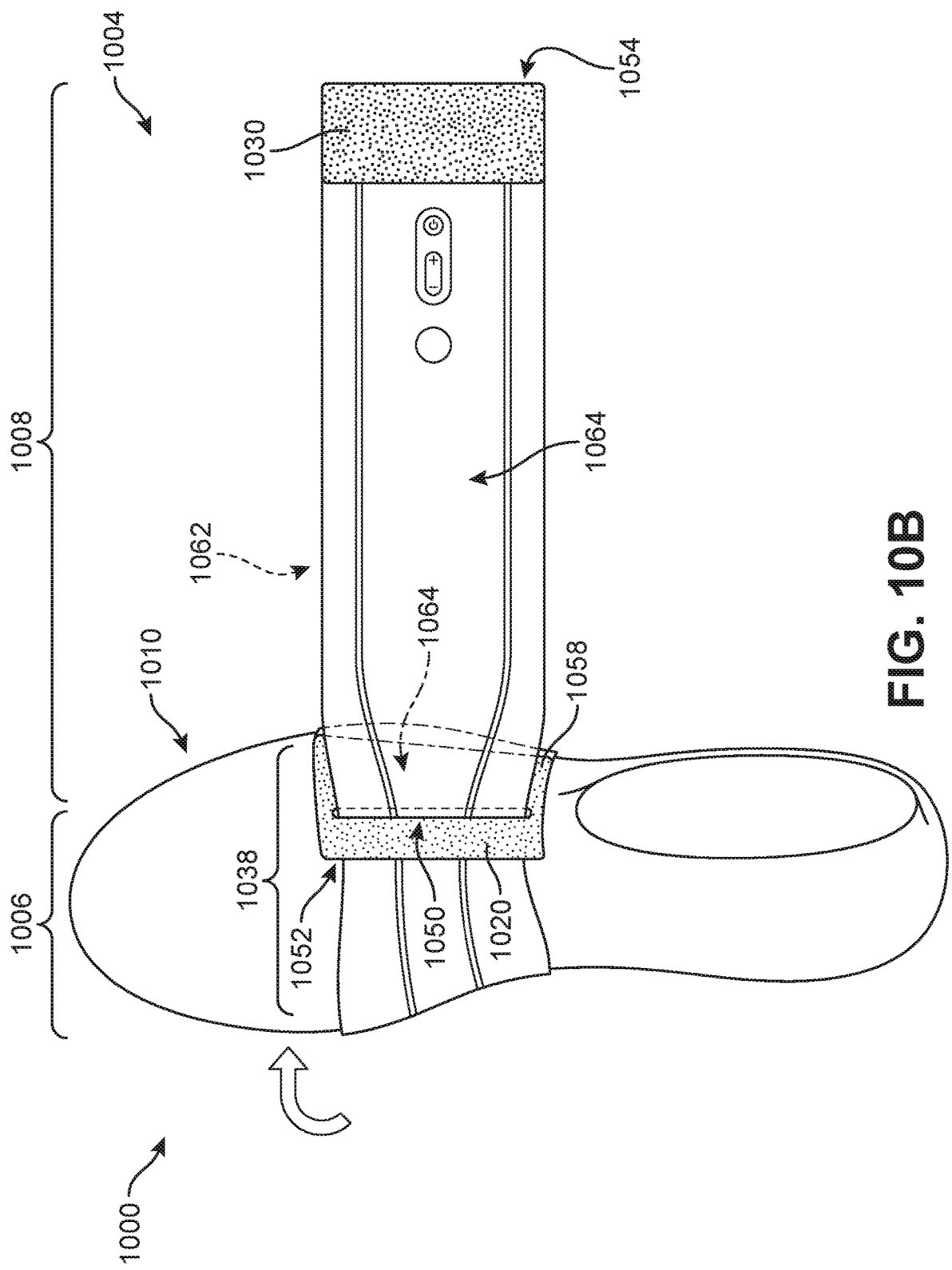

In some embodiments, the wrap appliance system can include further provisions for securing the wrap to a user's foot. In FIGS. 10A and 10B, one possible example is shown in which the wrap appliance also includes a securing mechanism that may be implemented upon completion of the first circuit around a foot. In FIG. 10A, a fifth compression appliance ("fifth appliance") 1000 is depicted. The sequence of FIGS. 10A and 10B presents an alternate wrapping process relative to FIGS. 3 and 4. In the example of FIG. 10A, in a first stage 1002, the fifth appliance 1000 is disposed and arranged in part beneath a foot 1010. More specifically, a first zone 1006 of the fifth appliance 1000 is positioned such that a first end 1052 is disposed at the user's desired starting point, here on a lateral side portion of the foot 1010 in the midfoot region, and a first zone 1006 of the wrap continues around and underneath foot 1010 (e.g., inner surface 1062 is pressed along or contacts the arch or sole of the foot), while a second zone 1008 of the wrap (terminating in a second end 1054) extends in a distal direction away from the foot. In other embodiments, the user may elect to begin the wrapping process in the opposite direction by rotation of the wrap approximately 180 degrees, such that the first end 1052 is disposed along the medial side of the foot and the remainder of the wrap instead extends toward the lateral side. Furthermore, the starting point (location where first end 1052 will be initially positioned) can vary widely around the foot (or other anatomical region) per the user's preferences. Thus, the specific descriptions of relative wrap location to the foot can vary from what is shown.

In FIG. 10A, the first end 1052 can be seen to be disposed on an outer edge of an end tab portion ("end portion") 1020 of the wrap. In addition, the end portion 1020 also includes a narrow opening, cut, aperture, or slot 1050, having a lateral width W5, extending in a direction between the upper edge and lower edge of the wrap. Furthermore, in an optional embodiment, the end tab portion 1050 can include an additional fastening mechanism 1058 as described previously, such as a hook and loop fastener material provided on the surface of the end portion 1020. A neck region ("neck portion" 1038) extends between the first zone 1006 and the second zone 1008 of the fifth appliance 1000, and is narrower relative to the width of the remainder of the wrap (e.g., see FIG. 2). The narrowest width of the neck portion 1038, in some embodiments associated with a central portion or midline of the neck portion 1038, can also be understood to have a lateral width W4 that is substantially similar or equal to width W5 of slot 1050. In addition, in some embodiments, a fastener region 1064 directly adjacent to the center of the neck portion 1038 can include a fastener mechanism that is complementary and/or configured for a releasable attachment to fastening mechanism 1058, as shown in FIG. 10B.

In FIG. 10B, during a second stage 1004, the first zone 1006 is pulled back toward the foot 1010 and its inner surface 1062 is pressed against the upper part of the foot from the medial side toward the lateral side, until the first end 1052 is in contact with a portion of the wrap. This completes a first full circuit of the foot, which also coincides with the full application of first zone 1006 around the foot. In other words, any subsequent wrapping of the foot will now be provided by the second zone 1008 of the wrap. Thus, as described earlier with respect to compression appliance 200 (see FIGS. 2-7), each zone of the fifth appliance 1000 may be understood to be configured to serve or correspond to a loop around the user's body part. In this case, the first zone 1006 corresponds to a first loop of the wrap, while the second zone 1008 will correspond to a second loop of the wrap.

Figure 6:
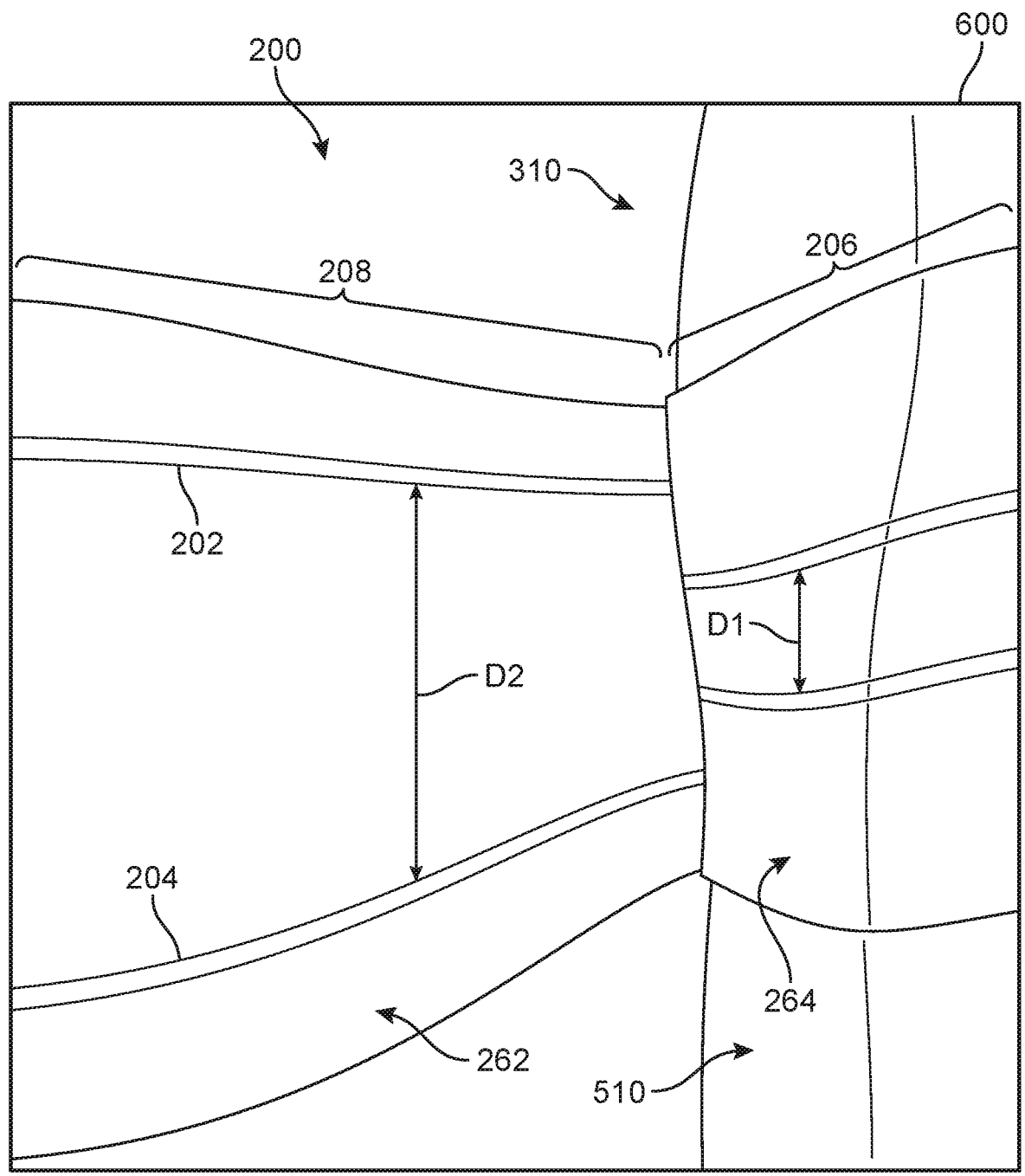
FIGS. 6 and 7 are a depiction of a wrapping stage of the compression appliance in which a second zone completes a circuit around the foot, overlapping the first zone.

However, in contrast to the previous embodiment, in this example, the first zone 1006 is passed through the slot 1050, until neck portion 1038 is extended partially through slot 1050. In order for the first zone 1006—which is wider than the slot width (W5)—to be pushed through the slot 1050, the user may crumple, scrunch, squish, or otherwise compress the first zone 1006 to permit its passage through the narrower slot 1050. The user will be able to readily observe that the initial circuit is complete once the wrap no longer needs to be compressed or scrunched in order to move through the slot 1050 (i.e., the first zone 1006 of the wrap has fully exited the slot 1050), and the narrowest region of neck portion 1038 now fits or is disposed snugly within the slot 1050 while permitting the remainder of the wrap to be smooth or flat again. Thus, the width of the neck portion 1038 is configured to match the width of the slot 1050 to facilitate the pass-through of an appropriate length of the wrap (i.e., first zone 1006) and ensure a smooth coupling or intersection between the two segments (i.e., end portion 1020 and neck portion 1038) that remains snugly wrapped until the user reverses the process by again scrunching the first zone 1006 and pulling the first zone 1006 out of the slot 1050. In some embodiments, the fastener region 1064 shown in FIG. 10A can also be secured to the corresponding portion of the end portion 1020 for a snug closure of the first circuit. In other words, the first circuit of the wrap is now further anchored into place around the user's foot, minimizing any sliding or other undesired movement of the end tab portion or loosening of the first circuit. The user can then continue to wrap the second zone 1008 of the fifth appliance 1000 around the foot (and around the first zone 1006), as shown in FIGS. 6 and 7.

Figure 11:
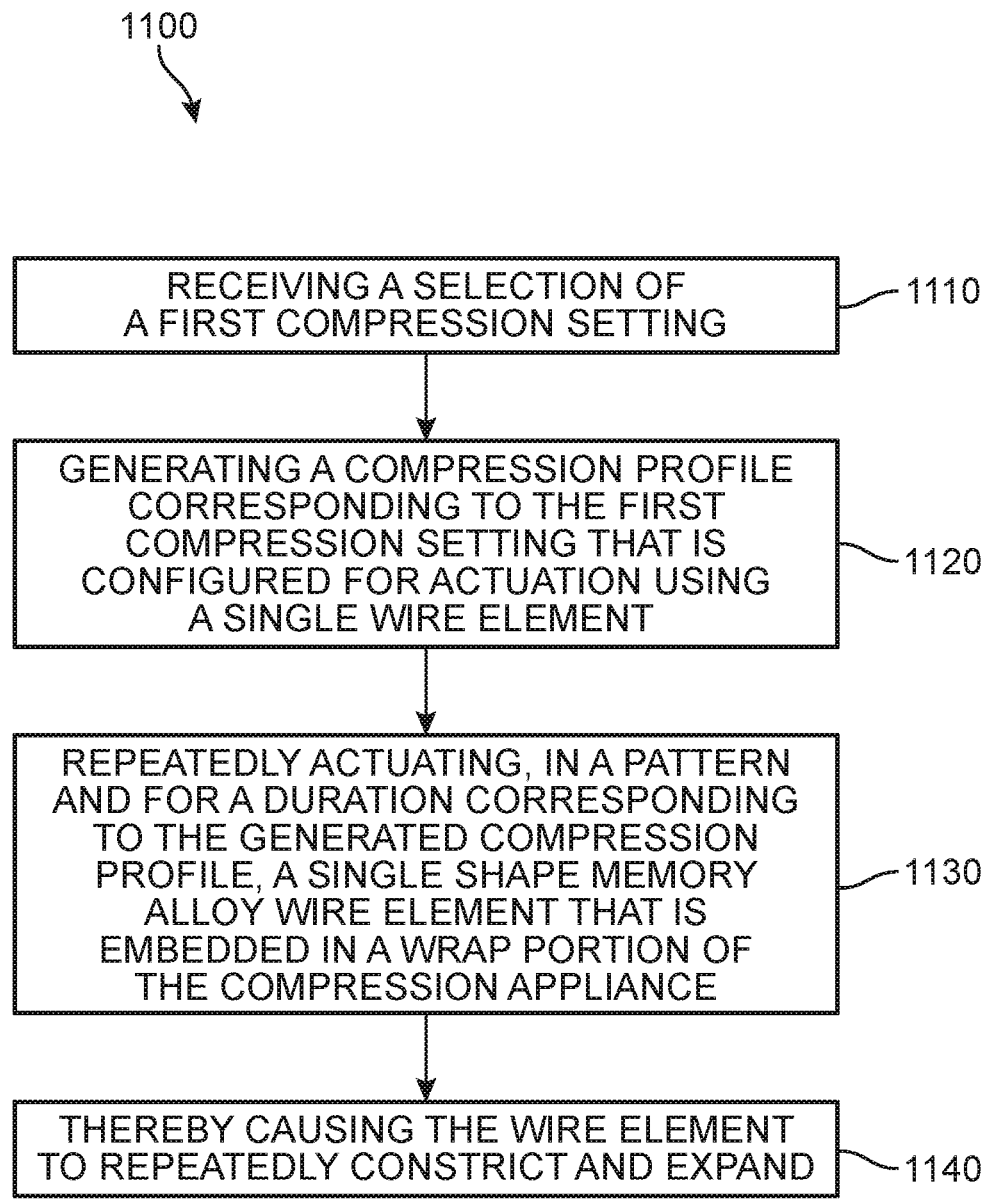
FIG. 11 is a flow chart presenting a method of using a compression appliance system, according to an embodiment.

FIG. 11 is a flow chart illustrating an embodiment of a method 1100 of using a compression appliance. The method 1100 includes a first step 1110 of receiving a selection of a first compression setting, and a second step 1120 of generating a compression profile corresponding to the first compression setting that is configured for actuation using a single wire element. A third step 1130 includes repeatedly actuating, in a pattern and for a duration corresponding to the generated compression profile, a single shape memory alloy wire element that is embedded in a wrap portion of the compression appliance, thereby causing, in a fourth step 1140, the single wire element to repeatedly constrict and expand.

In other embodiments, the method may include additional steps or aspects. For example, the wire element can be understood to extend across a full length of the wrap portion between a first end portion and a second end portion and loops back to extend a second time between the second end portion to the first end portion, such that actuation occurs along four separate pathways across the length of the wrap portion when the compression appliance is wrapped twice around an object. In another example, the first compression setting includes a selection of the duration for the actuation and/or a strength of the power to be applied during the actuation, or a selection of a compression pattern type, such as pulsing, cyclic, random, or ramping/gradated. In some cases, the compression profile includes repeatedly providing a varying amount of power to the single wire element, such that the predetermined amount of power gradually increases and gradually decreases during the first duration.

In different embodiments, other methods can be contemplated within the scope of the disclosure. Another method can include a first step of receiving a selection of a predetermined compression profile for the compression appliance. In this case, the compression appliance includes a single wire element, and the single wire element extending across a length of a wrap portion of the compression appliance between a first end portion to a second end portion and loops back to extend a second time across the length of the wrap portion from the second end portion to the first end portion. In other words, the wrap portion includes both an upper wire segment and a lower wire segment that are both made of the same, continuous wire element. The method further includes a second step of actuating the single wire element to apply a predetermined pattern of compressions corresponding to the selected predetermined compression profile in response to receiving the selection of the predetermined compression profile. In this case, the actuation occurs along four separate pathways across the length of the wrap portion when the compression appliance is wrapped twice around an object as described herein.

In some embodiments, this method can further include providing a predetermined amount of power to the single wire element for a first predetermined amount of time or duration, and then turning off the single wire element for a second predetermined amount of time when the first predetermined amount of time ends. This on/off cycle can be repeated for a selected overall activity duration. The first predetermined amount of time can be determined based on the selected predetermined compression profile selection.

The present application is directed to a compression appliance including a wire element configured to constrict upon actuation. The wire element, wrap, electronic assembly, and other features, components, or characteristics of the compression appliances described herein can make use of any of the principles, methods, systems, and teachings disclosed in any of the following applications: Wyatt et al., U.S. Pat. No. 9,326,911, issued May 3, 2016 and titled "Compression integument"; Wyatt et al., U.S. Patent Application Publication Number 2016/0374886, published Dec. 29, 2016 and titled "Compression Device"; Wyatt et al., U.S. Pat. No. 10,441,491, issued Oct. 15, 2019 and titled "Compression device"; Wyatt et al., U.S. Patent Application Publication Number 2018/0055009, published Mar. 1, 2018 and titled "Soothing garment for pets"; Rizzo et al., U.S. Patent Application Publication Number 2019/0274372, published Sep. 12, 2019 and titled "Systems and method for compression control in a wearable compression device"; Stasey et al., U.S. Pat. No. 10,188,152, issued Jan. 29, 2019 and titled "System for minimizing multi-dimensional breast displacement"; Wyatt et al., U.S. Patent Application Publication Number 2017/0252252, published Sep. 7, 2017 and titled "Compression Device"; Wyatt et al., U.S. Patent Application Publication Number 2017/0202276, published Jul. 20, 2017 and titled "System for Minimizing Multi-Dimensional Displacement of the Body"; Wyatt et al., U.S. Patent Application Publication Number 2019/0261744, published Aug. 29, 2019 and titled "Lace Tightener Incorporating SMA Wire"; and Wyatt et al., U.S. Patent Application Publication Number 2015/0065930, published Mar. 5, 2015 and titled "Compression Integument," the entirety of each application being herein incorporated by reference.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A wearable compression appliance comprising:
   an elongated wrap portion extending longitudinally between a first end portion and a second end portion of the compression appliance, the wrap portion including a first zone and a second zone, wherein the first zone includes the first end portion and the second zone includes the second end portion;
   a wire element, the wire element being a single continuous length of wire embedded in the wrap portion in a looped arrangement such that the wire element includes both a single continuous upper wire segment that extends along a longitudinal length and entirely above a longitudinal midline of the wrap portion and a single continuous lower wire segment that extends along the longitudinal length and entirely below the longitudinal midline of the wrap portion, and the single continuous upper wire segment is spaced apart from the single continuous lower wire segment such that the single continuous upper wire segment and the single continuous lower wire segment are parallel to each other in the first zone and the second zone; and
   wherein a first distance between the single continuous upper wire segment and the single continuous lower wire segment in the first zone is smaller than a second distance between the single continuous upper wire segment and the single continuous lower wire segment in the second zone, and wherein the wire element transitions between the first and second zones via a single inclined portion above the longitudinal midline and a single inclined portion below the longitudinal midline.

2. The compression appliance of claim 1, further comprising an electronic assembly that includes a controller configured to actuate the wire element and reduce an effective length of the wire element.

3. The compression appliance of claim 2, wherein the controller is configured to:
   apply a current to the wire element to reduce the effective length of the wire element; and
   remove the current to cause the wire element to return to an initial length.

4. The compression appliance of claim 2, wherein the controller is retained within a pocket in the wrap portion.

5. The compression appliance of claim 1, further comprising a neck region disposed between the first zone and the second zone of the wrap portion, the neck region including a first lateral width that is smaller than a width of both the first zone and the second zone.

6. The compression appliance of claim 5, wherein the first end portion further comprising a slot that includes a second lateral width that is equal to the first lateral width, the slot being configured to receive the neck region of the wrap portion.

7. The compression appliance of claim 5, wherein spacing between the upper wire segment and the lower wire segment widens from the first distance to the second distance at the neck region.

8. The compression appliance of claim 1, wherein, when the compression appliance is wrapped around a body part, four pathways of compressive stimulation are provided.

9. The compression appliance of claim 8, wherein the four pathways of compressive stimulation are defined by the upper wire segment in the first zone, the upper wire segment in the second zone, the lower wire segment in the first zone, and the lower wire segment in the second zone.

10. The compression appliance of claim 1, wherein the wire element comprises a shape-memory alloy material.

11. The compression appliance of claim 1, further comprising an electronic assembly disposed in a housing unit embedded at least partially in the second end portion.

12. The compression appliance of claim 1, wherein the upper wire segment and lower wire segment are joined together at a loop terminus embedded in the first end portion.

13. The compression appliance of claim 1, wherein the second zone has a greater length than the first zone.

14. The compression appliance of claim 1, wherein the first zone and second zone are designed to overlap when the compression appliance is wrapped around a body part while the wire element extending through the first zone remains spaced apart from the wire element in the second zone.

15. The compression appliance of claim 1, wherein the wrap portion comprises an elastic textile material.

16. The compression appliance of claim 1, further comprising a control interface embedded in the wrap portion, the control interface including selectable buttons configured to instruct a microprocessor to implement a predetermined sequence and pattern of compression based on a selected compression profile.

17. The compression appliance of claim 1, wherein the upper wire segment and the lower wire segment are arranged symmetrically about the longitudinal midline.

18. The compression appliance of claim 1, wherein the upper wire segment and the lower wire segment extend entirely along the longitudinal length of the wrap portion.

19. The compression appliance of claim 1, wherein the elongated wrap portion is a textile possessing a continuous surface from the first end portion to the second end portion.

20. A wearable compression appliance comprising:
an elongated wrap extending longitudinally between a first end portion and a second end portion, the elongated wrap defining a plurality of continuous zones, the plurality of continuous zones including a first zone and a second zone, wherein the first zone includes the first end portion and the second zone includes the second end portion;
a single wire element, the single wire element being a single continuous length of wire embedded in the elongated wrap and provided in a looped arrangement such that the single wire element includes:
  a continuous upper wire portion that extends along a longitudinal length of the elongated wrap, wherein the upper wire portion:
    extends continuously from the first end portion to the second end portion, and
    is positioned above a longitudinal midline of the elongated wrap across each of the first end portion, the first zone, the second zone and the second end portion; and
  a continuous lower wire portion that extends along the longitudinal length of the elongated wrap, the lower wire portion:
    extends continuously from the second end portion to the first end portion, and
    is positioned below the longitudinal midline of the elongated wrap across each of the second end portion, the second zone, the first zone and the first end portion;
wherein the upper wire portion is spaced apart from the lower wire portion such that the upper wire portion and the lower wire portion are oriented parallel to each other in each of the first zone and the second zone, and a first distance between the upper wire portion and the lower wire portion in the first zone is smaller than a second distance between the upper wire portion and the lower wire portion in the second zone, and wherein the wire element transitions between the first and second zones via a single inclined portion above the longitudinal midline and a single inclined portion below the longitudinal midline.

* * * * *